US010131883B2

(12) United States Patent
Hong et al.

(10) Patent No.: US 10,131,883 B2
(45) Date of Patent: Nov. 20, 2018

(54) DIKETOREDUCTASE MUTANT AND APPLICATION THEREOF

(71) Applicants: ASYMCHEM LABORATORIES (TIANJIN) CO., LTD., Tianjin (CN); ASYMCHEM LIFE SCIENCE (TIANJIN) CO., LTD., Tianjin (CN); TIANJIN ASYMCHEM PHARMACEUTICAL CO., LTD., Tianjin (CN); ASYMCHEM LABORATORIES (FUXIN) CO., LTD., Fuxin (CN); JILIN ASYMCHEM LABORATORIES CO., LTD., Dunhua (CN)

(72) Inventors: Hao Hong, Tianjin (CN); James Gage, Tianjin (CN); Feng Gao, Tianjin (CN); Lihui Liu, Tianjin (CN); Wenyan Yu, Tianjin (CN); Fang Liu, Tianjin (CN); Lina Guo, Tianijn (CN); Na Zhang, Tianjin (CN)

(73) Assignees: Asymchem Laboratories (Tianjin) Co., Ltd, Tianjin (CN); Asymchem Life Science (Tianjin) Co., Ltd, Tianjin (CN); Tianjin Asymchem Pharmaceutical Co., Ltd, Tianjin (CN); Asymchem Laboratories (Fuxin) Co., Ltd, Fuxin (CN); Jilin Asymchem Laboratories Co., Ltd, Dunhua (CN)

( * ) Notice: Subject to any disclaimer, the term of this patent is extended or adjusted under 35 U.S.C. 154(b) by 0 days.

(21) Appl. No.: 15/309,690

(22) PCT Filed: Aug. 4, 2014

(86) PCT No.: PCT/CN2014/083648
§ 371 (c)(1),
(2) Date: Nov. 8, 2016

(87) PCT Pub. No.: WO2015/168999
PCT Pub. Date: Nov. 12, 2015

(65) Prior Publication Data
US 2017/0152488 A1 Jun. 1, 2017

(30) Foreign Application Priority Data

May 9, 2014 (CN) .......................... 2014 1 0196920

(51) Int. Cl.
C12N 9/04 (2006.01)
C12N 15/53 (2006.01)
C12P 7/62 (2006.01)
C12N 5/10 (2006.01)
C12N 15/63 (2006.01)

(52) U.S. Cl.
CPC ............. *C12N 9/0006* (2013.01); *C12N 5/10* (2013.01); *C12N 15/63* (2013.01); *C12P 7/62* (2013.01); *C12Y 101/01184* (2013.01)

(58) Field of Classification Search
CPC .................................................. C12N 9/0006
See application file for complete search history.

(56) References Cited

FOREIGN PATENT DOCUMENTS

| CN | 101429514 A | 5/2009 |
|----|-------------|--------|
| CN | 101880694 A | 11/2010 |
| CN | 102277338 A | 12/2011 |
| CN | 102517241 A | 6/2012 |
| CN | 103937759 A | 7/2014 |
| CN | 103937761 A | 7/2014 |
| WO | WO 2015/168999 A1 | 6/2012 |

OTHER PUBLICATIONS

Machine translation of CN102277338, published Dec. 14, 2011, translated on Oct. 27, 2017 (Year: 2011).*
GenBank accession No. WP_007730327.1 GenBank database Jun. 5, 2013 (Jun. 5, 2013).
International Search Report and Written Opinion for PCT/CN2014/083648 dated Feb. 13, 2015.
CN Application No. 201410196920.5, Third Office Action dated Dec. 13, 2016.
GenBank: : Accession No. WP_003943259, "glutamine amidotransferase [Rhodococcus erythropolis]," May 26, 2013. [Retrieved from the Internet Jul. 18, 2018: <URL: https://www.ncbi.nlm.nih.gov/protein/WP_003943259.1>].
EP 14891354.4 Extended European Search Report dated Aug. 22, 2017.
Huang, et al., "Identification of important residues in diketoreductas from *Acinetobacter baylyi* by molecular modeling and site-directed mutagenesis," *Biochimie*, 94:471-478 (2012).
Huang, et al., "Functional roles of Tryptophan residues in diketoreductase from Acinetobacter baylyi," *BMB Reports*, 45(8):452-457 (2012).
Kumar, et al., "Draft Genome Sequence of Rhodococcus triatomae Strain BKS 15-14," Genome Announcements, vol. 1, Issue2, e00129-13, (2013).
Sekine, et al., "Sequence analysis of three plasmids harboured in Rhodococcus erythropolis strain PR4," *Environmental Microbiology*, 8(2):334-346, (2006).
Shevtsov, et al., "Draft Genome Sequence of Rhodococcus erythropolis DNI, a Crude Oil Biodegrader," *Genome Announcements*, vol. 1, Issue 5, e-00846-13, (2013).

(Continued)

*Primary Examiner* — Rebecca E Prouty
(74) *Attorney, Agent, or Firm* — Alston & Bird LLP

(57) ABSTRACT

The application provides a Diketoreductase (DKR) mutant, its nucleotide coding sequence, and an expression cassette, recombinant vector and host cell containing the sequence, as well as a method for application of the mutant to the preparation of 3R,5S-dicarbonyl compound. An ee value of the obtained 3R,5S-dicarbonyl compound is higher than 99%, and a de value is about 90%. The DKR mutant is a key pharmaceutical intermediate, and particularly provides an efficient catalyst for synthesis of a chiral dicarbonyl hexanoic acid chain of a statin drug.

7 Claims, 3 Drawing Sheets
Specification includes a Sequence Listing.

(56) References Cited

OTHER PUBLICATIONS

PCT/CN2014/083648 International Preliminary Report on Patentability dated Nov. 15, 2016.
PCT/CN2014/083648 International Search Report, English translation, dated Feb. 13, 2015.
PCT/CN2014/083648 Written Opinion of the International Searching Authority, English translation, dated Feb. 13, 2015.

* cited by examiner

SEQUENCE LISTING

```
<160> NUMBER OF SEQ ID NOS: 56

<210> SEQ ID NO 1
<211> LENGTH: 286
<212> TYPE: PRT
<213> ORGANISM: Artificial Sequence
<220> FEATURE:
<223> OTHER INFORMATION: diketoreductase mutant

<400> SEQUENCE: 1

Met Thr Glu Leu Lys Gln Ile Thr Val Leu Gly Thr Gly Val Leu Gly
1               5                   10                  15

Ser Gln Ile Ala Tyr Gln Thr Ala Cys His Gly Phe Asp Val Val Ala
            20                  25                  30

Tyr Asp Ile Asn Ala Glu Val Ile Glu Lys Ala Lys Ala Arg Phe Asp
        35                  40                  45

Ser Leu Ala Ala Ala Tyr Lys Ala Glu Asn Val Glu Gly Ala Lys Glu
    50                  55                  60

Gly Lys Ala Asp Glu Ala Leu Gln Arg Ile Thr Tyr Ser Tyr Asp Leu
65                  70                  75                  80

Gly Glu Ala Val Ala Lys Ala Asp Leu Val Ile Glu Ala Ile Pro Glu
                85                  90                  95

Asp Ile Ala Ile Lys Arg Asp Thr Tyr Glu Lys Leu Ala Thr Val Ala
            100                 105                 110

Pro Glu His Thr Val Phe Ala Thr Asn Ser Ser Thr Leu Leu Pro Ser
        115                 120                 125
```

```
Asp Leu Lys Glu Phe Thr Gly Arg Pro Glu Lys Phe Leu Ala Leu His
    130                 135                 140

Phe Ala Asn His Val Trp Val Asn Asn Thr Ala Glu Val Met Gly Thr
145                 150                 155                 160

Glu Ser Thr Asp Pro Ala Val Tyr Arg Glu Val Glu Phe Ala Lys
                165                 170                 175

Asn Ile Gly Met Val Pro Ile Glu Leu Lys Lys Glu Lys Ala Gly Tyr
                180                 185                 190

Val Leu Asn Ser Leu Leu Val Pro Leu Leu Asn Ala Ala Ser Asp Leu
                195                 200                 205

Leu Ile Asp Gly Ile Ala Asp Pro Asp Met Val Asp Lys Thr Trp Arg
    210                 215                 220

Ile Gly Thr Gly Ala Pro Trp Gly Pro Phe Gln Ile Met Asp Val Val
225                 230                 235                 240

Gly Leu Thr Thr Val Tyr Asn Ile Ser Ser Gln Gly Gly Glu Lys Gln
                245                 250                 255

Arg Glu Phe Ala Asp Tyr Ile Lys Lys Asn Tyr Ile Asp Glu Gly Lys
                260                 265                 270

Leu Gly Val Ala Val Gly Asp Gly Phe Tyr Asn Tyr Lys Gly
                275                 280                 285

<210> SEQ ID NO 2
<211> LENGTH: 286
<212> TYPE: PRT
<213> ORGANISM: artificial
<220> FEATURE:
<223> OTHER INFORMATION: diketoreductase mutant

<400> SEQUENCE: 2

Met Thr Glu Leu Lys Gln Ile Thr Val Leu Gly Thr Gly Val Leu Gly
1               5                   10                  15

Ser Gln Ile Ala Tyr Gln Thr Ala Cys His Gly Phe Asp Val Val Ala
                20                  25                  30

Tyr Asp Ile Asn Ala Glu Val Ile Glu Lys Ala Lys Ala Arg Phe Asp
                35                  40                  45

Ser Leu Ala Ala Ala Tyr Lys Ala Glu Asn Val Glu Gly Ala Lys Glu
    50                  55                  60

Gly Lys Ala Asp Glu Ala Leu Gln Arg Ile Thr Tyr Ser Tyr Asp Leu
65                  70                  75                  80

Gly Glu Ala Val Ala Lys Ala Asp Leu Val Ile Glu Ala Val Pro Glu
                85                  90                  95

Asp Ile Ala Ile Lys Arg Asp Thr Tyr Glu Lys Leu Ala Thr Val Ala
                100                 105                 110

Pro Glu His Thr Val Phe Ala Thr Asn Ser Ser Thr Leu Leu Pro Ser
                115                 120                 125

Asp Leu Lys Glu Phe Thr Gly Arg Pro Glu Lys Phe Leu Ala Leu His
    130                 135                 140

Phe Ala Asn His Val Trp Val Asn Asn Thr Ala Glu Val Met Gly Thr
145                 150                 155                 160

Glu Ser Thr Asp Pro Ala Val Tyr Arg Glu Val Glu Phe Ala Lys
                165                 170                 175

Asn Ile Gly Met Val Pro Ile Glu Leu Lys Lys Glu Lys Ala Gly Tyr
                180                 185                 190

Val Leu Asn Ser Leu Leu Val Pro Leu Leu Asn Ala Ala Ser Asp Leu
                195                 200                 205
```

-continued

```
Leu Ile Asp Gly Ile Ala Asp Pro Asp Met Val Asp Lys Thr Trp Arg
    210                 215                 220
Ile Gly Thr Gly Ala Pro Trp Gly Pro Phe Gln Ile Met Asp Val Val
225                 230                 235                 240
Gly Leu Thr Thr Val Tyr Asn Ile Ser Ser Gln Gly Gly Glu Lys Gln
                245                 250                 255
Arg Glu Phe Ala Asp Tyr Ile Lys Lys Asn Tyr Ile Asp Glu Gly Lys
            260                 265                 270
Leu Gly Val Ala Val Gly Asp Gly Phe Tyr Asn Tyr Lys Gly
        275                 280                 285
```

<210> SEQ ID NO 3
<211> LENGTH: 286
<212> TYPE: PRT
<213> ORGANISM: artificial
<220> FEATURE:
<223> OTHER INFORMATION: diketoreductase mutant

<400> SEQUENCE: 3

```
Met Thr Glu Leu Lys Gln Ile Thr Val Leu Gly Thr Gly Val Leu Gly
1               5                   10                  15
Ser Gln Ile Ala Tyr Gln Thr Ala Cys His Gly Phe Asp Val Val Ala
                20                  25                  30
Tyr Asp Ile Asn Ala Glu Val Ile Glu Lys Ala Lys Ala Arg Phe Asp
            35                  40                  45
Ser Leu Ala Ala Ala Tyr Lys Ala Glu Asn Val Glu Gly Ala Lys Glu
        50                  55                  60
Gly Lys Ala Asp Glu Ala Leu Gln Arg Ile Thr Tyr Ser Tyr Asp Leu
65                  70                  75                  80
Gly Glu Ala Val Ala Lys Ala Asp Leu Val Ile Glu Ala Val Pro Glu
                85                  90                  95
Asp Ile Ala Ile Lys Arg Asp Thr Tyr Glu Lys Leu Ala Thr Val Ala
            100                 105                 110
Pro Glu His Thr Val Phe Ala Thr Asn Ser Ser Thr Leu Leu Pro Ser
        115                 120                 125
Asp Leu Lys Glu Phe Thr Gly Arg Pro Glu Lys Phe Leu Ala Leu His
    130                 135                 140
Phe Ala Asn His Val Trp Gln Asn Asn Thr Ala Glu Val Met Gly Thr
145                 150                 155                 160
Glu Ser Thr Asp Pro Ala Val Tyr Arg Glu Val Val Glu Phe Ala Lys
                165                 170                 175
Asn Ile Gly Met Val Pro Ile Glu Leu Lys Lys Glu Lys Ala Gly Tyr
            180                 185                 190
Val Leu Asn Ser Leu Leu Val Pro Leu Leu Asn Ala Ala Ser Asp Leu
        195                 200                 205
Leu Ile Asp Gly Ile Ala Asp Pro Asp Met Val Asp Lys Thr Trp Arg
    210                 215                 220
Ile Gly Thr Gly Ala Pro Trp Gly Pro Phe Gln Ile Met Asp Val Val
225                 230                 235                 240
Gly Leu Thr Thr Val Tyr Asn Ile Ser Ser Gln Gly Gly Glu Lys Gln
                245                 250                 255
Arg Glu Phe Ala Asp Tyr Ile Lys Lys Asn Tyr Ile Asp Glu Gly Lys
            260                 265                 270
Leu Gly Val Ala Val Gly Asp Gly Phe Tyr Asn Tyr Lys Gly
        275                 280                 285
```

<210> SEQ ID NO 4
<211> LENGTH: 286
<212> TYPE: PRT
<213> ORGANISM: artificial
<220> FEATURE:
<223> OTHER INFORMATION: diketoreductase mutant

<400> SEQUENCE: 4

```
Met Thr Glu Leu Lys Gln Ile Thr Val Leu Gly Thr Gly Val Leu Gly
1               5                   10                  15

Ser Gln Ile Ala Tyr Gln Thr Ala Cys His Gly Phe Asp Val Val Ala
            20                  25                  30

Tyr Asp Ile Asn Ala Glu Val Ile Glu Lys Ala Lys Ala Arg Phe Asp
        35                  40                  45

Ser Leu Ala Ala Ala Tyr Lys Ala Glu Asn Val Glu Gly Ala Lys Glu
    50                  55                  60

Gly Lys Ala Asp Glu Ala Leu Gln Arg Ile Thr Tyr Ser Tyr Asp Leu
65                  70                  75                  80

Gly Glu Ala Val Ala Lys Ala Asp Leu Val Ile Glu Ala Ile Pro Glu
                85                  90                  95

Asp Ile Ala Ile Lys Arg Asp Thr Tyr Glu Lys Leu Ala Thr Val Ala
            100                 105                 110

Pro Glu His Thr Val Phe Ala Thr Asn Ser Ser Thr Leu Leu Pro Ser
        115                 120                 125

Asp Leu Lys Glu Phe Thr Gly Arg Pro Glu Lys Phe Leu Ala Leu His
    130                 135                 140

Phe Ala Asn His Val Trp Val Asn Asn Thr Ala Glu Val Met Gly Thr
145                 150                 155                 160

Glu Ser Thr Asp Pro Ala Val Tyr Arg Glu Val Val Glu Phe Ala Lys
                165                 170                 175

Asn Ile Gly Met Val Pro Ile Glu Leu Lys Lys Glu Lys Ala Gly Tyr
            180                 185                 190

Val Leu Asn Ser Leu Leu Val Pro Leu Leu Asn Ala Ala Ser Asp Leu
        195                 200                 205

Leu Ile Asp Gly Ile Ala Asp Pro Asp Met Val Asp Lys Thr Trp Arg
    210                 215                 220

Ile Gly Thr Gly Ala Pro Phe Gly Pro Phe Gln Ile Met Asp Ile Val
225                 230                 235                 240

Gly Leu Thr Thr Val Tyr Asn Ile Ser Ser Gln Gly Gly Lys Gln
                245                 250                 255

Lys Glu Phe Ala Asp Tyr Ile Lys Lys Asn Tyr Ile Asp Glu Gly Lys
            260                 265                 270

Leu Gly Val Ala Val Gly Asp Gly Phe Tyr Asn Tyr Lys Gly
        275                 280                 285
```

<210> SEQ ID NO 5
<211> LENGTH: 286
<212> TYPE: PRT
<213> ORGANISM: artificial
<220> FEATURE:
<223> OTHER INFORMATION: diketoreductase mutant

<400> SEQUENCE: 5

```
Met Thr Glu Leu Lys Gln Ile Thr Val Leu Gly Thr Gly Val Leu Gly
1               5                   10                  15

Ser Gln Ile Ala Tyr Gln Thr Ala Cys His Gly Phe Asp Val Val Ala
            20                  25                  30
```

Tyr Asp Ile Asn Ala Glu Val Ile Glu Lys Ala Lys Ala Arg Phe Asp
            35                  40                  45

Ser Leu Ala Ala Ala Tyr Lys Ala Glu Asn Val Glu Gly Ala Lys Glu
        50                  55                  60

Gly Lys Ala Asp Glu Ala Leu Gln Arg Ile Thr Tyr Ser Tyr Asp Leu
65                  70                  75                  80

Gly Glu Ala Val Ala Lys Ala Asp Leu Val Ile Glu Ala Ile Pro Glu
                85                  90                  95

Asp Ile Ala Ile Lys Arg Asp Thr Tyr Glu Lys Leu Ala Thr Val Ala
            100                 105                 110

Pro Glu His Thr Val Phe Ala Thr Asn Ser Ser Thr Leu Leu Pro Ser
        115                 120                 125

Asp Leu Lys Glu Phe Thr Gly Arg Pro Glu Lys Phe Leu Ala Leu His
    130                 135                 140

Phe Ala Asn His Val Trp Gln Asn Asn Thr Ala Glu Val Met Gly Thr
145                 150                 155                 160

Glu Ser Thr Asp Pro Ala Val Tyr Arg Glu Val Val Glu Phe Ala Lys
                165                 170                 175

Asn Ile Gly Met Val Pro Ile Glu Leu Lys Lys Glu Lys Ala Gly Tyr
            180                 185                 190

Val Leu Asn Ser Leu Leu Val Pro Leu Leu Asn Ala Ala Ser Asp Leu
        195                 200                 205

Leu Ile Asp Gly Ile Ala Asp Pro Asp Met Val Asp Lys Thr Trp Arg
    210                 215                 220

Ile Gly Thr Gly Ala Pro Phe Gly Pro Phe Gln Ile Met Asp Val Val
225                 230                 235                 240

Gly Leu Thr Thr Val Tyr Asn Ile Ser Ser Gln Gly Gly Glu Lys Gln
                245                 250                 255

Lys Glu Phe Ala Asp Tyr Ile Lys Lys Asn Tyr Ile Asp Glu Gly Lys
            260                 265                 270

Leu Gly Val Ala Val Gly Asp Gly Phe Tyr Asn Tyr Lys Gly
        275                 280                 285

<210> SEQ ID NO 6
<211> LENGTH: 286
<212> TYPE: PRT
<213> ORGANISM: artificial
<220> FEATURE:
<223> OTHER INFORMATION: diketoreductase mutant

<400> SEQUENCE: 6

Met Thr Glu Leu Lys Gln Ile Thr Val Leu Gly Thr Gly Val Leu Gly
1               5                   10                  15

Ser Gln Ile Ala Tyr Gln Thr Ala Cys His Gly Phe Asp Val Val Ala
            20                  25                  30

Tyr Asp Ile Asn Ala Glu Val Ile Glu Lys Ala Lys Ala Arg Phe Asp
        35                  40                  45

Ser Leu Ala Ala Ala Tyr Lys Ala Glu Asn Val Glu Gly Ala Lys Glu
    50                  55                  60

Gly Lys Ala Asp Glu Ala Leu Gln Arg Ile Thr Tyr Ser Tyr Asp Leu
65                  70                  75                  80

Gly Glu Ala Val Ala Lys Ala Asp Leu Val Ile Glu Ala Val Pro Glu
                85                  90                  95

Asp Ile Ala Ile Lys Arg Asp Thr Tyr Glu Lys Leu Ala Thr Val Ala
            100                 105                 110

```
Pro Glu His Thr Val Phe Ala Thr Asn Ser Ser Thr Leu Leu Pro Ser
        115                 120                 125

Asp Leu Lys Glu Phe Thr Gly Arg Pro Glu Lys Phe Leu Ala Leu His
        130                 135                 140

Phe Ala Asn His Val Trp Gln Asn Asn Thr Ala Glu Val Met Gly Thr
145                 150                 155                 160

Glu Ser Thr Asp Pro Ala Val Tyr Arg Glu Val Val Glu Phe Ala Lys
                165                 170                 175

Asn Ile Gly Met Val Pro Ile Glu Leu Lys Lys Glu Lys Ala Gly Tyr
                180                 185                 190

Val Leu Asn Ser Leu Leu Val Pro Leu Leu Asn Ala Ala Ser Asp Leu
        195                 200                 205

Leu Ile Asp Gly Ile Ala Asp Pro Asp Met Val Asp Lys Thr Trp Arg
        210                 215                 220

Ile Gly Thr Gly Ala Pro Phe Gly Pro Phe Gln Ile Met Asp Val Val
225                 230                 235                 240

Gly Leu Thr Thr Val Tyr Asn Ile Ser Ser Gln Gly Gly Glu Lys Gln
                245                 250                 255

Arg Glu Phe Ala Asp Tyr Ile Lys Lys Asn Tyr Ile Glu Gly Lys
                260                 265                 270

Leu Gly Val Ala Val Gly Asp Gly Phe Tyr Asn Tyr Lys Gly
        275                 280                 285

<210> SEQ ID NO 7
<211> LENGTH: 286
<212> TYPE: PRT
<213> ORGANISM: rhodococcus erythropolis

<400> SEQUENCE: 7

Met Thr Glu Leu Lys Gln Ile Thr Val Leu Gly Thr Gly Val Leu Gly
1               5                   10                  15

Ser Gln Ile Ala Tyr Gln Thr Ala Cys His Gly Phe Asp Val Val Ala
            20                  25                  30

Tyr Asp Ile Asn Ala Glu Val Ile Glu Lys Ala Lys Ala Arg Phe Asp
        35                  40                  45

Ser Leu Ala Ala Ala Tyr Lys Ala Glu Asn Val Glu Gly Ala Lys Glu
    50                  55                  60

Gly Lys Ala Asp Glu Ala Leu Gln Arg Ile Thr Tyr Ser Tyr Asp Leu
65                  70                  75                  80

Gly Glu Ala Val Ala Lys Ala Asp Leu Val Ile Glu Ala Ile Pro Glu
                85                  90                  95

Asp Ile Ala Ile Lys Arg Asp Thr Tyr Glu Lys Leu Ala Thr Val Ala
            100                 105                 110

Pro Glu His Thr Val Phe Ala Thr Asn Ser Ser Thr Leu Leu Pro Ser
        115                 120                 125

Asp Leu Lys Glu Phe Thr Gly Arg Pro Glu Lys Phe Leu Ala Leu His
        130                 135                 140

Phe Ala Asn His Val Trp Val Asn Asn Thr Ala Glu Val Met Gly Thr
145                 150                 155                 160

Glu Ser Thr Asp Pro Ala Val Tyr Arg Glu Val Val Glu Phe Ala Lys
                165                 170                 175

Asn Ile Gly Met Val Pro Ile Glu Leu Lys Lys Glu Lys Ala Gly Tyr
                180                 185                 190

Val Leu Asn Ser Leu Leu Val Pro Leu Leu Asn Ala Ala Ser Asp Leu
```

195                 200                 205
Leu Ile Asp Gly Ile Ala Asp Pro Asp Met Val Asp Lys Thr Trp Arg
    210                 215                 220

Ile Gly Thr Gly Ala Pro Phe Gly Pro Phe Gln Ile Met Asp Val Val
225                 230                 235                 240

Gly Leu Thr Thr Val Tyr Asn Ile Ser Ser Gln Gly Gly Glu Lys Gln
                245                 250                 255

Arg Glu Phe Ala Asp Tyr Ile Lys Lys Asn Tyr Ile Asp Glu Gly Lys
            260                 265                 270

Leu Gly Val Ala Val Gly Asp Gly Phe Tyr Asn Tyr Lys Gly
        275                 280                 285

<210> SEQ ID NO 8
<211> LENGTH: 861
<212> TYPE: DNA
<213> ORGANISM: rhodococcus erythropolis

<400> SEQUENCE: 8

| | |
|---|---|
| atgactgaac tgaagcagat caccgttctg ggtaccggag ttctcggctc acagatcgcc | 60 |
| tatcagaccg cctgtcacgg tttcgacgtc gtcgcgtacg acatcaacgc cgaggtcatc | 120 |
| gaaaaggcca aggctcggtt cgactcgttg gccgcggcct acaaggccga aacgtcgag | 180 |
| ggtgccaagg aaggcaaggc tgacgaagcg ctgcaacgta ttacgtactc gtacgatcta | 240 |
| ggcgaagccg tcgccaaggc cgacctggtc atcgaggcaa ttcccgagga catcgccatc | 300 |
| aagcgcgaca cctacgagaa gcttgccacg gttgctcctg agcacacggt gttcgctacc | 360 |
| aactcctcga cgctgctgcc gagcgatctc aaggagttca ccggccgtcc cgagaagttc | 420 |
| ctcgcactgc acttcgcaaa tcacgtgtgg gtcaacaaca ctgccgaggt catgggcacc | 480 |
| gagtccaccg accccgccgt gtaccgcgag gtcgtcgagt tcgcgaagaa catcggcatg | 540 |
| gtgccgatcg aactcaagaa ggagaaggcg ggctacgtac tcaactcgct cctggtcccg | 600 |
| ctcctcaacg cggcctccga cctgctgatc gacggcatcg ccgatcccga catggtcgac | 660 |
| aagacgtggc gtatcggcac cggagccccg ttcggcccct tccagatcat ggacgtcgtc | 720 |
| gggttgacca ccgtctacaa catctcctcc cagggcggcg agaagcagcg cgaattcgcc | 780 |
| gactacatca agaagaacta catcgacgag ggcaagctcg gcgttgctgt cggcgacggc | 840 |
| ttctacaact acaagggctg a | 861 |

<210> SEQ ID NO 9
<211> LENGTH: 861
<212> TYPE: DNA
<213> ORGANISM: artificial
<220> FEATURE:
<223> OTHER INFORMATION: diketoreductase mutant coding sequence

<400> SEQUENCE: 9

| | |
|---|---|
| atgactgaac tgaagcagat caccgttctg ggtaccggag ttctcggctc acagatcgcc | 60 |
| tatcagaccg cctgtcacgg tttcgacgtc gtcgcgtacg acatcaacgc cgaggtcatc | 120 |
| gaaaaggcca aggctcggtt cgactcgttg gccgcggcct acaaggccga aacgtcgag | 180 |
| ggtgccaagg aaggcaaggc tgacgaagcg ctgcaacgta ttacgtactc gtacgatcta | 240 |
| ggcgaagccg tcgccaaggc cgacctggtc atcgaggcaa ttcccgagga catcgccatc | 300 |
| aagcgcgaca cctacgagaa gcttgccacg gttgctcctg agcacacggt gttcgctacc | 360 |
| aactcctcga cgctgctgcc gagcgatctc aaggagttca ccggccgtcc cgagaagttc | 420 |

```
ctcgcactgc acttcgcaaa tcacgtgtgg gtcaacaaca ctgccgaggt catgggcacc      480
gagtccaccg accccgccgt gtaccgcgag tcgtcgagt tcgcgaagaa catcggcatg       540
gtgccgatcg aactcaagaa ggagaaggcg ggctacgtac tcaactcgct cctggtcccg      600
ctcctcaacg cggcctccga cctgctgatc gacggcatcg ccgatcccga catggtcgac      660
aagacgtggc gtatcggcac cggagccccg tggggcccct tccagatcat ggacgtcgtc      720
gggttgacca ccgtctacaa catctcctcc cagggcggcg agaagcagcg cgaattcgcc      780
gactacatca agaagaacta catcgacgag ggcaagctcg cgttgctgt cggcgacggc       840 ttctacaact acaagggctg a                                                861
```

<210> SEQ ID NO 10
<211> LENGTH: 861
<212> TYPE: DNA
<213> ORGANISM: artificial
<220> FEATURE:
<223> OTHER INFORMATION: diketoreductase mutant coding sequence
<220> FEATURE:
<221> NAME/KEY: misc_feature
<222> LOCATION: (282)..(282)
<223> OTHER INFORMATION: n is a, c, g, or t

<400> SEQUENCE: 10

```
atgactgaac tgaagcagat caccgttctg ggtaccggag ttctcggctc acagatcgcc      60
tatcagaccg cctgtcacgg tttcgacgtc gtcgcgtacg acatcaacgc cgaggtcatc     120
gaaaaggcca aggctcggtt cgactcgttg gccgcggcct acaaggccga gaacgtcgag     180
ggtgccaagg aaggcaaggc tgacgaagcg ctgcaacgta ttacgtactc gtacgatcta     240
ggcgaagccg tcgccaaggc cgacctggtc atcgaggcag tncccgagga catcgccatc     300
aagcgcgaca cctacgagaa gcttgccacg gttgctcctg agcacacggt gttcgctacc     360
aactcctcga cgctgctgcc gagcgatctc aaggagttca ccggccgtcc cgagaagttc     420
ctcgcactgc acttcgcaaa tcacgtgtgg gtcaacaaca ctgccgaggt catgggcacc     480
gagtccaccg accccgccgt gtaccgcgag tcgtcgagt tcgcgaagaa catcggcatg     540
gtgccgatcg aactcaagaa ggagaaggcg ggctacgtac tcaactcgct cctggtcccg    600
ctcctcaacg cggcctccga cctgctgatc gacggcatcg ccgatcccga catggtcgac    660
aagacgtggc gtatcggcac cggagccccg tggggcccct tccagatcat ggacgtcgtc    720
gggttgacca ccgtctacaa catctcctcc cagggcggcg agaagcagcg cgaattcgcc    780
gactacatca agaagaacta catcgacgag ggcaagctcg cgttgctgt cggcgacggc     840 ttctacaact acaagggctg a                                               861
```

<210> SEQ ID NO 11
<211> LENGTH: 861
<212> TYPE: DNA
<213> ORGANISM: artificial
<220> FEATURE:
<223> OTHER INFORMATION: diketoreductase mutant coding sequence
<220> FEATURE:
<221> NAME/KEY: misc_feature
<222> LOCATION: (253)..(253)
<223> OTHER INFORMATION: r = g or a
<220> FEATURE:
<221> NAME/KEY: misc_feature
<222> LOCATION: (282)..(282)
<223> OTHER INFORMATION: n is a, c, g, or t

<400> SEQUENCE: 11

```
atgactgaac tgaagcagat caccgttctg ggtaccggag ttctcggctc acagatcgcc      60
```

```
tatcagaccg cctgtcacgg tttcgacgtc gtcgcgtacg acatcaacgc cgaggtcatc    120
gaaaaggcca aggctcggtt cgactcgttg gccgcggcct acaaggccga gaacgtcgag    180
ggtgccaagg aaggcaaggc tgacgaagcg ctgcaacgta ttacgtactc gtacgatcta    240
ggcgaagccg tcgccaaggc cgacctggtc atcgaggcag tncccgagga catcgccatc    300
aagcgcgaca cctacgagaa gcttgccacg gttgctcctg agcacacggt gttcgctacc    360
aactcctcga cgctgctgcc gagcgatctc aaggagttca ccggccgtcc cgagaagttc    420
ctcgcactgc acttcgcaaa tcacgtgtgg caaacaaca ctgccgaggt catgggcacc     480
gagtccaccg accccgccgt gtaccgcgag gtcgtcgagt tcgcgaagaa catcggcatg    540
gtgccgatcg aactcaagaa ggagaaggcg ggctacgtac tcaactcgct cctggtcccg    600
ctcctcaacg cggcctccga cctgctgatc gacggcatcg ccgatcccga catggtcgac    660
aagacgtggc gtatcggcac cggagccccg tggggcccct tccagatcat ggacgtcgtc    720
gggttgacca ccgtctacaa catctcctcc cagggcggcg agaagcagcg cgaattcgcc    780
gactacatca agaagaacta catcgacgag ggcaagctcg gcgttgctgt cggcgacggc    840
ttctacaact acaagggctg a                                              861
```

```
<210> SEQ ID NO 12
<211> LENGTH: 861
<212> TYPE: DNA
<213> ORGANISM: artificial
<220> FEATURE:
<223> OTHER INFORMATION: diketoreductase mutant coding sequence
<220> FEATURE:
<221> NAME/KEY: misc_feature
<222> LOCATION: (717)..(717)
<223> OTHER INFORMATION: h = a, c, t/u
<220> FEATURE:
<221> NAME/KEY: misc_feature
<222> LOCATION: (771)..(771)
<223> OTHER INFORMATION: r = g or a

<400> SEQUENCE: 12
atgactgaac tgaagcagat caccgttctg ggtaccggag ttctcggctc acagatcgcc     60
tatcagaccg cctgtcacgg tttcgacgtc gtcgcgtacg acatcaacgc cgaggtcatc    120
gaaaaggcca aggctcggtt cgactcgttg gccgcggcct acaaggccga gaacgtcgag    180
ggtgccaagg aaggcaaggc tgacgaagcg ctgcaacgta ttacgtactc gtacgatcta    240
ggcgaagccg tcgccaaggc cgacctggtc atcgaggcaa ttcccgagga catcgccatc    300
aagcgcgaca cctacgagaa gcttgccacg gttgctcctg agcacacggt gttcgctacc    360
aactcctcga cgctgctgcc gagcgatctc aaggagttca ccggccgtcc cgagaagttc    420
ctcgcactgc acttcgcaaa tcacgtgtgg gtcaacaaca ctgccgaggt catgggcacc    480
gagtccaccg accccgccgt gtaccgcgag gtcgtcgagt tcgcgaagaa catcggcatg    540
gtgccgatcg aactcaagaa ggagaaggcg ggctacgtac tcaactcgct cctggtcccg    600
ctcctcaacg cggcctccga cctgctgatc gacggcatcg ccgatcccga catggtcgac    660
aagacgtggc gtatcggcac cggagccccg ttcggcccct tccagatcat ggacathgtc    720
gggttgacca ccgtctacaa catctcctcc cagggcggcg agaagcagaa rgaattcgcc    780
gactacatca agaagaacta catcgacgag ggcaagctcg gcgttgctgt cggcgacggc    840
ttctacaact acaagggctg a                                              861
```

```
<210> SEQ ID NO 13
```

```
<211> LENGTH: 861
<212> TYPE: DNA
<213> ORGANISM: artificial
<220> FEATURE:
<223> OTHER INFORMATION: diketoreductase mutant coding sequence
<220> FEATURE:
<221> NAME/KEY: misc_feature
<222> LOCATION: (453)..(453)
<223> OTHER INFORMATION: r = g or a
<220> FEATURE:
<221> NAME/KEY: misc_feature
<222> LOCATION: (771)..(771)
<223> OTHER INFORMATION: r = g or a

<400> SEQUENCE: 13
atgactgaac tgaagcagat caccgttctg ggtaccggag ttctcggctc acagatcgcc     60
tatcagaccg cctgtcacgg tttcgacgtc gtcgcgtacg acatcaacgc cgaggtcatc    120
gaaaaggcca aggctcggtt cgactcgttg gccgcggcct acaaggccga aacgtcgag     180 ggtgccaagg aaggcaaggc tgacgaagcg ctgcaacgta ttacgtactc gtacgatcta    240
ggcgaagccg tcgccaaggc cgacctggtc atcgaggcaa ttcccgagga catcgccatc    300
aagcgcgaca cctacgagaa gcttgccacg gttgctcctg agcacacggt gttcgctacc    360
aactcctcga cgctgctgcc gagcgatctc aaggagttca ccggccgtcc cgagaagttc    420
ctcgcactgc acttcgcaaa tcacgtgtgg caraacaaca ctgccgaggt catgggcacc    480
gagtccaccg accccgccgt gtaccgcgag gtcgtcgagt cgcgaagaa catcggcatg    540 gtgccgatcg aactcaagaa ggagaaggcg ggctacgtac tcaactcgct cctggtcccg    600
ctcctcaacg cggcctccga cctgctgatc gacggcatcg ccgatcccga catggtcgac    660
aagacgtggc gtatcggcac cggagccccg ttcggcccct ccagatcat ggacgtcgtc    720 gggttgacca ccgtctacaa catctcctcc cagggcggcg agaagcagaa rgaattcgcc    780
gactacatca agaagaacta catcgacgag ggcaagctcg gcgttgctgt cggcgacggc    840
ttctacaact acaagggctg a                                              861

<210> SEQ ID NO 14
<211> LENGTH: 861
<212> TYPE: DNA
<213> ORGANISM: artificial
<220> FEATURE:
<223> OTHER INFORMATION: diketoreductase mutant coding sequence
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (453)..(453)
<223> OTHER INFORMATION: r = g or a

<400> SEQUENCE: 14
atgactgaac tgaagcagat caccgttctg ggtaccggag ttctcggctc acagatcgcc     60
tatcagaccg cctgtcacgg tttcgacgtc gtcgcgtacg acatcaacgc cgaggtcatc    120
gaaaaggcca aggctcggtt cgactcgttg gccgcggcct acaaggccga aacgtcgag     180 ggtgccaagg aaggcaaggc tgacgaagcg ctgcaacgta ttacgtactc gtacgatcta    240
ggcgaagccg tcgccaaggc cgacctggtc atcgaggcag tncccgagga catcgccatc    300
aagcgcgaca cctacgagaa gcttgccacg gttgctcctg agcacacggt gttcgctacc    360
aactcctcga cgctgctgcc gagcgatctc aaggagttca ccggccgtcc cgagaagttc    420
ctcgcactgc acttcgcaaa tcacgtgtgg caraacaaca ctgccgaggt catgggcacc    480
```

```
gagtccaccg acccccgccgt gtaccgcgag gtcgtcgagt tcgcgaagaa catcggcatg    540
gtgccgatcg aactcaagaa ggagaaggcg ggctacgtac tcaactcgct cctggtcccg    600
ctcctcaacg cggcctccga cctgctgatc gacggcatcg ccgatcccga catggtcgac    660
aagacgtggc gtatcggcac cggagccccg ttcggcccct tccagatcat ggacgtcgtc    720
gggttgacca ccgtctacaa catctcctcc cagggcggcg agaagcagcg cgaattcgcc    780
gactacatca agaagaacta catcgacgag ggcaagctcg gcgttgctgt cggcgacggc    840
ttctacaact acaagggctg a                                              861
```

```
<210> SEQ ID NO 15
<211> LENGTH: 29
<212> TYPE: DNA
<213> ORGANISM: artificial
<220> FEATURE:
<223> OTHER INFORMATION: I94-Forward Primer
<220> FEATURE:
<221> NAME/KEY: misc_feature
<222> LOCATION: (14)..(16)
<223> OTHER INFORMATION: n is a, c, g, or t

<400> SEQUENCE: 15
ggtcatcgag gcannncccg aggacatcg                                       29

<210> SEQ ID NO 16
<211> LENGTH: 29
<212> TYPE: DNA
<213> ORGANISM: artificial
<220> FEATURE:
<223> OTHER INFORMATION: I94-Reverse Primer
<220> FEATURE:
<221> NAME/KEY: misc_feature
<222> LOCATION: (14)..(16)
<223> OTHER INFORMATION: n is a, c, g, or t

<400> SEQUENCE: 16
cgatgtcctc gggnnntgcc tcgatgacc                                       29

<210> SEQ ID NO 17
<211> LENGTH: 38
<212> TYPE: DNA
<213> ORGANISM: artificial
<220> FEATURE:
<223> OTHER INFORMATION: E96-Forward Primer
<220> FEATURE:
<221> NAME/KEY: misc_feature
<222> LOCATION: (19)..(21)
<223> OTHER INFORMATION: n is a, c, g, or t

<400> SEQUENCE: 17
gtcatcgagg caattcccnn ngacatcgcc atcaagcg                             38

<210> SEQ ID NO 18
<211> LENGTH: 38
<212> TYPE: DNA
<213> ORGANISM: artificial
<220> FEATURE:
<223> OTHER INFORMATION: E96-Reverse
<220> FEATURE:
<221> NAME/KEY: misc_feature
<222> LOCATION: (18)..(20)
<223> OTHER INFORMATION: n is a, c, g, or t

<400> SEQUENCE: 18
cgcttgatgg cgatgtcnnn gggaattgcc tcgatgac                             38
```

<210> SEQ ID NO 19
<211> LENGTH: 40
<212> TYPE: DNA
<213> ORGANISM: artificial
<220> FEATURE:
<223> OTHER INFORMATION: R102-Forward Primer
<220> FEATURE:
<221> NAME/KEY: misc_feature
<222> LOCATION: (19)..(21)
<223> OTHER INFORMATION: n is a, c, g, or t

<400> SEQUENCE: 19
gaggacatcg ccatcaagnn ngacacctac gagaagcttg                40

<210> SEQ ID NO 20
<211> LENGTH: 40
<212> TYPE: DNA
<213> ORGANISM: artificial
<220> FEATURE:
<223> OTHER INFORMATION: R102-Reverse Primer
<220> FEATURE:
<221> NAME/KEY: misc_feature
<222> LOCATION: (20)..(22)
<223> OTHER INFORMATION: n is a, c, g, or t

<400> SEQUENCE: 20
caagcttctc gtaggtgtcn nncttgatgg cgatgtcctc                40

<210> SEQ ID NO 21
<211> LENGTH: 30
<212> TYPE: DNA
<213> ORGANISM: artificial
<220> FEATURE:
<223> OTHER INFORMATION: T124-Forward Primer
<220> FEATURE:
<221> NAME/KEY: misc_feature
<222> LOCATION: (15)..(17)
<223> OTHER INFORMATION: n is a, c, g, or t

<400> SEQUENCE: 21
ctaccaactc ctcgnnnctg ctgccgagcg                30

<210> SEQ ID NO 22
<211> LENGTH: 30
<212> TYPE: DNA
<213> ORGANISM: artificial
<220> FEATURE:
<223> OTHER INFORMATION: T124-Reverse Primer
<220> FEATURE:
<221> NAME/KEY: misc_feature
<222> LOCATION: (14)..(16)
<223> OTHER INFORMATION: n is a, c, g, or t

<400> SEQUENCE: 22
cgctcggcag cagnnncgag gagttggtag                30

<210> SEQ ID NO 23
<211> LENGTH: 30
<212> TYPE: DNA
<213> ORGANISM: artificial
<220> FEATURE:
<223> OTHER INFORMATION: S123-Forward Primer
<220> FEATURE:
<221> NAME/KEY: misc_feature
<222> LOCATION: (14)..(16)
<223> OTHER INFORMATION: n is a, c, g, or t

<400> SEQUENCE: 23
cgctaccaac tccnnnacgc tgctgccgag                30

<210> SEQ ID NO 24
<211> LENGTH: 30
<212> TYPE: DNA
<213> ORGANISM: artificial
<220> FEATURE:
<223> OTHER INFORMATION: S123-Reverse Primer
<220> FEATURE:
<221> NAME/KEY: misc_feature
<222> LOCATION: (15)..(17)
<223> OTHER INFORMATION: n is a, c, g, or t

<400> SEQUENCE: 24
ctcggcagca gcgtnnngga gttggtagcg                                          30

<210> SEQ ID NO 25
<211> LENGTH: 27
<212> TYPE: DNA
<213> ORGANISM: artificial
<220> FEATURE:
<223> OTHER INFORMATION: H148-Forward Primer
<220> FEATURE:
<221> NAME/KEY: misc_feature
<222> LOCATION: (13)..(15)
<223> OTHER INFORMATION: n is a, c, g, or t

<400> SEQUENCE: 25
cacttcgcaa atnnngtgtg ggtcaac                                             27

<210> SEQ ID NO 26
<211> LENGTH: 28
<212> TYPE: DNA
<213> ORGANISM: artificial
<220> FEATURE:
<223> OTHER INFORMATION: H148-Reverse Primer
<220> FEATURE:
<221> NAME/KEY: misc_feature
<222> LOCATION: (13)..(15)
<223> OTHER INFORMATION: n is a, c, g, or t

<400> SEQUENCE: 26
gttgacccac acnnnatttg cgaagtgg                                            28

<210> SEQ ID NO 27
<211> LENGTH: 29
<212> TYPE: DNA
<213> ORGANISM: artificial
<220> FEATURE:
<223> OTHER INFORMATION: V151-Forward Primer
<220> FEATURE:
<221> NAME/KEY: misc_feature
<222> LOCATION: (15)..(17)
<223> OTHER INFORMATION: n is a, c, g, or t

<400> SEQUENCE: 27
caaatcacgt gtggnnnaac aacactgcc                                           29

<210> SEQ ID NO 28
<211> LENGTH: 29
<212> TYPE: DNA
<213> ORGANISM: artificial
<220> FEATURE:
<223> OTHER INFORMATION: V151-Reverse Primer
<220> FEATURE:
<221> NAME/KEY: misc_feature
<222> LOCATION: (13)..(15)
<223> OTHER INFORMATION: n is a, c, g, or t

<400> SEQUENCE: 28
ggcagtgttg ttnnnccaca cgtgatttg                                29

<210> SEQ ID NO 29
<211> LENGTH: 29
<212> TYPE: DNA
<213> ORGANISM: artificial
<220> FEATURE:
<223> OTHER INFORMATION: E156-Forward Primer
<220> FEATURE:
<221> NAME/KEY: misc_feature
<222> LOCATION: (14)..(16)
<223> OTHER INFORMATION: n is a, c, g, or t

<400> SEQUENCE: 29
caacaacact gccnnngtca tgggcaccg                                29

<210> SEQ ID NO 30
<211> LENGTH: 29
<212> TYPE: DNA
<213> ORGANISM: artificial
<220> FEATURE:
<223> OTHER INFORMATION: E156-Reverse Primer
<220> FEATURE:
<221> NAME/KEY: misc_feature
<222> LOCATION: (14)..(16)
<223> OTHER INFORMATION: n is a, c, g, or t

<400> SEQUENCE: 30
cggtgcccat gacnnnggca gtgttgttg                                29

<210> SEQ ID NO 31
<211> LENGTH: 33
<212> TYPE: DNA
<213> ORGANISM: artificial
<220> FEATURE:
<223> OTHER INFORMATION: K189-Forward Primer
<220> FEATURE:
<221> NAME/KEY: misc_feature
<222> LOCATION: (16)..(18)
<223> OTHER INFORMATION: n is a, c, g, or t

<400> SEQUENCE: 31
gaactcaaga aggagnnngc gggctacgta ctc                           33

<210> SEQ ID NO 32
<211> LENGTH: 33
<212> TYPE: DNA
<213> ORGANISM: artificial
<220> FEATURE:
<223> OTHER INFORMATION: K189-Reverse Primer
<220> FEATURE:
<221> NAME/KEY: misc_feature
<222> LOCATION: (16)..(18)
<223> OTHER INFORMATION: n is a, c, g, or t

<400> SEQUENCE: 32
gagtacgtag cccgcnnnct ccttcttgag ttc                           33

<210> SEQ ID NO 33
<211> LENGTH: 40
<212> TYPE: DNA
<213> ORGANISM: artificial
<220> FEATURE:
<223> OTHER INFORMATION: G191-Forward Primer
<220> FEATURE:
<221> NAME/KEY: misc_feature
<222> LOCATION: (22)..(24)
<223> OTHER INFORMATION: n is a, c, g, or t

<400> SEQUENCE: 33
gaactcaaga aggagaaggc gnnntacgta ctcaactcgc        40

<210> SEQ ID NO 34
<211> LENGTH: 40
<212> TYPE: DNA
<213> ORGANISM: artificial
<220> FEATURE:
<223> OTHER INFORMATION: G191-Reverse Primer
<220> FEATURE:
<221> NAME/KEY: misc_feature
<222> LOCATION: (17)..(19)
<223> OTHER INFORMATION: n is a, c, g, or t

<400> SEQUENCE: 34
gcgagttgag tacgtannnc gccttctcct tcttgagttc        40

<210> SEQ ID NO 35
<211> LENGTH: 27
<212> TYPE: DNA
<213> ORGANISM: artificial
<220> FEATURE:
<223> OTHER INFORMATION: L194-Forward Primer
<220> FEATURE:
<221> NAME/KEY: misc_feature
<222> LOCATION: (12)..(14)
<223> OTHER INFORMATION: n is a, c, g, or t

<400> SEQUENCE: 35
cgggctacgt annnaactcg ctcctgg        27

<210> SEQ ID NO 36
<211> LENGTH: 27
<212> TYPE: DNA
<213> ORGANISM: artificial
<220> FEATURE:
<223> OTHER INFORMATION: L194-Reverse Primer
<220> FEATURE:
<221> NAME/KEY: misc_feature
<222> LOCATION: (14)..(16)
<223> OTHER INFORMATION: n is a, c, g, or t

<400> SEQUENCE: 36
ccaggagcga gttnnntacg tagcccg        27

<210> SEQ ID NO 37
<211> LENGTH: 30
<212> TYPE: DNA
<213> ORGANISM: artificial
<220> FEATURE:
<223> OTHER INFORMATION: W223-Forward Primer
<220> FEATURE:
<221> NAME/KEY: misc_feature
<222> LOCATION: (14)..(16)
<223> OTHER INFORMATION: n is a, c, g, or t

<400> SEQUENCE: 37
ggtcgacaag acgnnncgta tcggcaccgg        30

<210> SEQ ID NO 38
<211> LENGTH: 30
<212> TYPE: DNA
<213> ORGANISM: artificial
<220> FEATURE:
<223> OTHER INFORMATION: W223-Reverse Primer
<220> FEATURE:
<221> NAME/KEY: misc_feature
<222> LOCATION: (15)..(17)
<223> OTHER INFORMATION: n is a, c, g, or t

<400> SEQUENCE: 38
ccggtgccga tacgnnncgt cttgtcgacc                                           30

<210> SEQ ID NO 39
<211> LENGTH: 40
<212> TYPE: DNA
<213> ORGANISM: artificial
<220> FEATURE:
<223> OTHER INFORMATION: F231-Forward Primer
<220> FEATURE:
<221> NAME/KEY: misc_feature
<222> LOCATION: (20)..(22)
<223> OTHER INFORMATION: n is a, c, g, or t

<400> SEQUENCE: 39
tatcggcacc ggagccccgn nnggcccctt ccagatcatg                                 40

<210> SEQ ID NO 40
<211> LENGTH: 40
<212> TYPE: DNA
<213> ORGANISM: artificial
<220> FEATURE:
<223> OTHER INFORMATION: F231-Reverse Primer
<220> FEATURE:
<221> NAME/KEY: misc_feature
<222> LOCATION: (19)..(21)
<223> OTHER INFORMATION: n is a, c, g, or t

<400> SEQUENCE: 40
catgatctgg aaggggccnn ncggggctcc ggtgccgata                                 40

<210> SEQ ID NO 41
<211> LENGTH: 32
<212> TYPE: DNA
<213> ORGANISM: artificial
<220> FEATURE:
<223> OTHER INFORMATION: M237-Forward Primer
<220> FEATURE:
<221> NAME/KEY: misc_feature
<222> LOCATION: (15)..(17)
<223> OTHER INFORMATION: n is a, c, g, or t

<400> SEQUENCE: 41
gccccttcca gatcnnngac gtcgtcgggt tg                                        32

<210> SEQ ID NO 42
<211> LENGTH: 32
<212> TYPE: DNA
<213> ORGANISM: artificial
<220> FEATURE:
<223> OTHER INFORMATION: M237-Reverse Primer
<220> FEATURE:
<221> NAME/KEY: misc_feature
<222> LOCATION: (16)..(18)
<223> OTHER INFORMATION: n is a, c, g, or t

<400> SEQUENCE: 42
caacccgacg acgtcnnnga tctggaaggg gc                                        32

<210> SEQ ID NO 43
<211> LENGTH: 33
<212> TYPE: DNA
<213> ORGANISM: artificial
<220> FEATURE:
<223> OTHER INFORMATION: V239-Forward Primer
<220> FEATURE:
<221> NAME/KEY: misc_feature
<222> LOCATION: (17)..(19)
<223> OTHER INFORMATION: n is a, c, g, or t -continued

<400> SEQUENCE: 43
cttccagatc atggacnnng tcgggttgac cac                               33

<210> SEQ ID NO 44
<211> LENGTH: 33
<212> TYPE: DNA
<213> ORGANISM: artificial
<220> FEATURE:
<223> OTHER INFORMATION: V239-Reverse Primer
<220> FEATURE:
<221> NAME/KEY: misc_feature
<222> LOCATION: (15)..(17)
<223> OTHER INFORMATION: n is a, c, g, or t

<400> SEQUENCE: 44
gtggtcaacc cgacnnngtc catgatctgg aag                               33

<210> SEQ ID NO 45
<211> LENGTH: 27
<212> TYPE: DNA
<213> ORGANISM: artificial
<220> FEATURE:
<223> OTHER INFORMATION: V240-Forward Primer
<220> FEATURE:
<221> NAME/KEY: misc_feature
<222> LOCATION: (14)..(16)
<223> OTHER INFORMATION: n is a, c, g, or t

<400> SEQUENCE: 45
gatcatggac gtcnnnpggt tgaccac                                      27

<210> SEQ ID NO 46
<211> LENGTH: 27
<212> TYPE: DNA
<213> ORGANISM: artificial
<220> FEATURE:
<223> OTHER INFORMATION: V240-Reverse Primer
<220> FEATURE:
<221> NAME/KEY: misc_feature
<222> LOCATION: (12)..(14)
<223> OTHER INFORMATION: n is a, c, g, or t

<400> SEQUENCE: 46
gtggtcaacc cnnngacgtc catgatc                                      27

<210> SEQ ID NO 47
<211> LENGTH: 29
<212> TYPE: DNA
<213> ORGANISM: artificial
<220> FEATURE:
<223> OTHER INFORMATION: N247-Forward Primer
<220> FEATURE:
<221> NAME/KEY: misc_feature
<222> LOCATION: (14)..(16)
<223> OTHER INFORMATION: n is a, c, g, or t

<400> SEQUENCE: 47
gaccaccgtc tacnnnatct cctcccagg                                    29

<210> SEQ ID NO 48
<211> LENGTH: 29
<212> TYPE: DNA
<213> ORGANISM: artificial
<220> FEATURE:
<223> OTHER INFORMATION: N247-Reverse Primer
<220> FEATURE:
<221> NAME/KEY: misc_feature
<222> LOCATION: (14)..(16)

```
<223> OTHER INFORMATION: n is a, c, g, or t

<400> SEQUENCE: 48
cctgggagga gatnnngtag acggtggtc                                             29

<210> SEQ ID NO 49
<211> LENGTH: 29
<212> TYPE: DNA
<213> ORGANISM: artificial
<220> FEATURE:
<223> OTHER INFORMATION: Q251-Forward Primer
<220> FEATURE:
<221> NAME/KEY: misc_feature
<222> LOCATION: (14)..(16)
<223> OTHER INFORMATION: n is a, c, g, or t

<400> SEQUENCE: 49
caacatctcc tccnnnggcg gcgagaagc                                             29

<210> SEQ ID NO 50
<211> LENGTH: 29
<212> TYPE: DNA
<213> ORGANISM: artificial
<220> FEATURE:
<223> OTHER INFORMATION: Q251-Reverse Primer
<220> FEATURE:
<221> NAME/KEY: misc_feature
<222> LOCATION: (14)..(16)
<223> OTHER INFORMATION: n is a, c, g, or t

<400> SEQUENCE: 50
gcttctcgcc gccnnnggag gagatgttg                                             29

<210> SEQ ID NO 51
<211> LENGTH: 44
<212> TYPE: DNA
<213> ORGANISM: artificial
<220> FEATURE:
<223> OTHER INFORMATION: R257-Forward Primer
<220> FEATURE:
<221> NAME/KEY: misc_feature
<222> LOCATION: (21)..(23)
<223> OTHER INFORMATION: n is a, c, g, or t

<400> SEQUENCE: 51
cccagggcgg cgagaagcag nnngaattcg ccgactacat caag                            44

<210> SEQ ID NO 52
<211> LENGTH: 44
<212> TYPE: DNA
<213> ORGANISM: artificial
<220> FEATURE:
<223> OTHER INFORMATION: R257-Reverse Primer
<220> FEATURE:
<221> NAME/KEY: misc_feature
<222> LOCATION: (22)..(24)
<223> OTHER INFORMATION: n is a, c, g, or t

<400> SEQUENCE: 52
cttgatgtag tcggcgaatt cnnnctgctt ctcgccgccc tggg                            44

<210> SEQ ID NO 53
<211> LENGTH: 31
<212> TYPE: DNA
<213> ORGANISM: artificial
<220> FEATURE:
<223> OTHER INFORMATION: L273-Forward Primer
<220> FEATURE:
<221> NAME/KEY: misc_feature
```

```
<222> LOCATION: (17)..(19)
<223> OTHER INFORMATION: n is a, c, g, or t

<400> SEQUENCE: 53
catcgacgag ggcaagnnng gcgttgctgt c                              31

<210> SEQ ID NO 54
<211> LENGTH: 31
<212> TYPE: DNA
<213> ORGANISM: artificial
<220> FEATURE:
<223> OTHER INFORMATION: L273-Reverse Primer
<220> FEATURE:
<221> NAME/KEY: misc_feature
<222> LOCATION: (13)..(15)
<223> OTHER INFORMATION: n is a, c, g, or t

<400> SEQUENCE: 54
gacagcaacg ccnnncttgc cctcgtcgat g                              31

<210> SEQ ID NO 55
<211> LENGTH: 40
<212> TYPE: DNA
<213> ORGANISM: artificial
<220> FEATURE:
<223> OTHER INFORMATION: A276-Forward Primer
<220> FEATURE:
<221> NAME/KEY: misc_feature
<222> LOCATION: (20)..(22)
<223> OTHER INFORMATION: n is a, c, g, or t

<400> SEQUENCE: 55
cgagggcaag ctcggcgttn nngtcggcga cggcttctac                     40

<210> SEQ ID NO 56
<211> LENGTH: 40
<212> TYPE: DNA
<213> ORGANISM: artificial
<220> FEATURE:
<223> OTHER INFORMATION: A276-Reverse Primer
<220> FEATURE:
<221> NAME/KEY: misc_feature
<222> LOCATION: (19)..(21)
<223> OTHER INFORMATION: n is a, c, g, or t

<400> SEQUENCE: 56
gtagaagccg tcgccgacnn naacgccgag cttgccctcg                     40
```

DIKETOREDUCTASE MUTANT AND APPLICATION THEREOF

CROSS-REFERENCE TO RELATED APPLICATIONS

This application is a national phase entry of International Application No. PCT/CN2014/083648, filed Aug. 4, 2014, which claims priority to CN 201410196920.5, filed May 9, 2014, the entire contents of each of which are incorporated herein by reference.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named SubSeqList.txt, created on Nov. 10, 2016, and having a size of 38 kilobytes and is filed on Nov. 10, 2016. The sequence listing contained in this ASCII formatted document is part of the specification and is herein incorporated by reference in its entirety.

TECHNICAL FIELD

The application relates to a Diketoreductase (DKR) mutant and an application thereof, and in particular to a DKR mutant obtained by site-directed saturation mutagenesis and of which properties such as catalytic activity are improved, and an application of the DKR mutant to preparation of a 3R,5S-dihydroxy compound.

BACKGROUND

Carbonyl reductase is a kind of oxidoreductase, and plays an important role in many biotransformation processes of biological organisms. Based on its capability in catalytically generating chiral alcohols with high enantioselectivity, the carbonyl reductase is usually applied as a very important biocatalyst to the synthesis of chiral intermediates in the chemical and pharmaceutical industries. DKR may stereoselectively reduce two carbonyls of a diketo acid ester simultaneously to give the corresponding hydroxyl, and it may be used for synthesizing key drug intermediates, particularly synthesizing a chiral dihydroxy hexanoic acid chain of a statin drug such as worldwide saleable cholesterol lowering drugs atorvastatin and rosuvastatin.

Currently known DKR can be used as a biocatalyst for reducing a diketone substrate in one step to prepare a chiral intermediate 3R,5S-dihydroxy-6-benzyloxy-tert-butyl hexanoate of a statin lipid-lowering drug with approximately single optical purity, thereby simplifying synthetic steps and reducing production pollution. However, application to industrial production still has some problems to be further solved. For example, low enzyme catalytic activity equates to a large amount of enzyme liquid and increased total volume of a reaction system, which increases production batches and production costs. These problems may be solved by directed evolution to improve catalytic activity of DKR. As a biocatalyst, an enzyme may fully develop its characteristics of high efficiency and high specificity in a biological system. However, there exist the common problems of inadaptability to an industrial production condition, low catalysis capability of an unnatural substrate and the like during industrial applications. Enzyme molecules are required to be modified to meet different application requirements by virtue of protein engineering methods. The protein engineering methods may be summarized into three: rational design, irrational design and semi-rational design.

Rational design refers to changing individual amino acids in protein molecules by virtue of site-directed mutagenesis or another methods on the basis of knowing the spatial structure of proteins, thereby generating proteins with new characters. This method is theoretically high in pertinence, and is mainly used for modifying catalytic activity of natural apoenzymes, substrate specificity and stability, changing an inhibitor type, coenzyme specificity and the like.

A site-directed saturation mutagenesis technology is an important technology in protein engineering, belongs to semi-rational design, but combines advantages of rational design and irrational design, overcomes respective shortcomings, and modifies a coding gene of a target protein to acquire a mutant of which an amino acid at a target site is substituted with other 19 amino acids respectively within a short time. This technology not only is a powerful tool for directed modification of proteins, but also is an important means for researching a protein's structure-function relationship. Researches show that multisite mutagenesis may always obtain an evolution more ideal than that obtained by single-site mutagenesis. Multisite mutagenesis is unlikely to be directly implemented by site-directed mutagenesis. However, site-directed saturation mutagenesis can increase the diversity of mutants and is simple to manipulate.

Therefore, if a site-directed saturation mutagenesis technology may be utilized to modify DKR to improve its catalytic activity and substrate specificity and/or stability, the problems of large amount of enzyme liquid, high production cost and the like in the prior art may be solved.

SUMMARY

In view of this, the application is intended to modify DKR by virtue of a site-directed saturation mutagenesis technology to improve its catalytic activity and substrate specificity and/or stability.

The first aspect of the application relates to a DKR mutant, which comprises one of amino acid sequences shown as follows:
  a) SEQ ID NO: 1 to SEQ ID NO:6;
  b) a sequence which has identity of at least 70% with the sequences shown in a) and has improved DKR activity; and
  c) a sequence which is obtained by deleting, adding and/or substituting one or more amino acid residues in the sequences in a) and has improved DKR activity,
  wherein the sequence shown in b) is not a sequence shown as SEQ ID NO: 7.

In one embodiment, the DKR mutant comprises the amino acid sequence shown as SEQ ID NO: 1, 2, 3, 4, 5 or 6.

In another embodiment, the DKR mutant comprises the amino acid sequence shown as SEQ ID NO: 1, 2 or 3.

In another embodiment, the DKR mutant comprises the amino acid sequence shown as SEQ ID NO: 2.

The second aspect of the application relates to a nucleotide coding sequence of the above mentioned DKR mutant, wherein the nucleotide coding sequence does not contain a sequence shown as SEQ ID NO: 8.

In an embodiment, the nucleotide coding sequence comprises a sequence shown as follows:
  a) sequences shown as SEQ ID NO: 9-14;
  b) a sequence which has identity of at least 70% with the sequences shown in a) and codes a protein with improved DKR activity; and c) a sequence which is hybridized with the sequences shown in a) under a highly stringent condition and codes a protein with improved DKR activity.

The third aspect of the application relates to an expression cassette comprising the above mentioned nucleotide coding sequence.

The fourth aspect of the application relates to a recombinant vector effectively linked with the nucleotide coding sequence, preferably, the recombinant vector is a recombinant expression vector.

The fifth aspect of the application relates to a host cell comprising the above mentioned recombinant vector.

The sixth aspect of the application relates to a method for producing a 3R,5S-dihydroxy compound, which includes the following steps: causing the above mentioned DKR mutant or a protein coded by the abovementioned nucleotide coding sequence or a protein obtained by virtue of the abovementioned expression cassette or the abovementioned recombinant vector or the abovementioned host cell to contact with a diketone compound under a condition of making DKR to act for a period of time, wherein the diketone compound is a commercial raw material on the market or an easy-to-prepare ketone compound with general formula I:

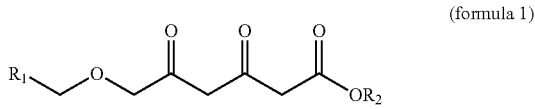

(formula 1)

where R1 is selected from an aromatic group, an alkyl group, a naphthenic base, an alkyl-substituted aromatic base, a halogen-substituted aryl, an aromatic heterocycl, a heterocycloalkyl or an alkyl-substituted heterocycloalkyl; and R2 is selected from an alkyl group, a naphthenic base, a haloalkyl group or a halogen naphthenic base.

In an embodiment, the diketone compound is selected from 6-benzyloxy-3,5-dioxo-tert-butyl hexanoate, 6-benzyloxy-3,5-dioxo-neopentyl hexanoate, 6-benzyloxy-3,5-dioxo-methyl hexanoate and 6-benzyloxy-3,5-dioxo-ethyl hexanoate.

In other words, the DKR mutant gene mutation with improved enzyme activity is obtained by a method of performing gene mutation by taking a DKR gene (shown as SEQ ID NO: 7) of a rhodococcuserythropolis SK121 strain as a parent gene and performing directed screening.

In the application, an amino acid sequence of the DKR mutant derived from the rhodococcuserythropolis SK121 strain includes the following sequences:

(1) an amino acid sequence shown as SEQ ID NO: 1: a mutation site is F231W:

MTELKQITVLGTGVLGSQIAYQTACHGFDVVAYDINAEVIEKAKARFDSL

AAAYKAENVEGAKEGKADEALQRITYSYDLGEAVAKADLVIEAIPEDIAI

KRDTYEKLATVAPEHTVFATNSSTLLPSDLKEFTGRPEKFLALHFANHVW

VNNTAEVMGTESTDPAVYREVVEFAKNIGMVPIELKKEKAGYVLNSLLVP

LLNAASDLLIDGIADPDMVDKTWRIGTGAPWGPFQIMDVVGLTTVYNISS

QGGEKQREFADYIKKNYIDEGKLGVAVGDGFYNYKG;

(2) an amino acid sequence shown as SEQ ID NO: 2: mutation sites are I94V+F231W:

MTELKQITVLGTGVLGSQIAYQTACHGFDVVAYDINAEVIEKAKARFDSL

AAAYKAENVEGAKEGKADEALQRITYSYDLGEAVAKADLVIEAVPEDIAI

KRDTYEKLATVAPEHTVFATNSSTLLPSDLKEFTGRPEKFLALHFANHVW

VNNTAEVMGTESTDPAVYREVVEFAKNIGMVPIELKKEKAGYVLNSLLVP

LLNAASDLLIDGIADPDMVDKTWRIGTGAPWGPFQIMDVVGLTTVYNISS

QGGEKQREFADYIKKNYIDEGKLGVAVGDGFYNYKG;

(3) an amino acid sequence shown as SEQ ID NO: 3: mutation sites are I94V+V151Q+F231W:

MTELKQITVLGTGVLGSQIAYQTACHGFDVVAYDINAEVIEKAKARFDSL

AAAYKAENVEGAKEGKADEALQRITYSYDLGEAVAKADLVIEAVPEDIAI

KRDTYEKLATVAPEHTVFATNSSTLLPSDLKEFTGRPEKFLALHFANHVW

QNNTAEVMGTESTDPAVYREVVEFAKNIGMVPIELKKEKAGYVLNSLLVP

LLNAASDLLIDGIADPDMVDKTWRIGTGAPWGPFQIMDVVGLTTVYNISS

QGGEKQREFADYIKKNYIDEGKLGVAVGDGFYNYKG;

(4) an amino acid sequence shown as SEQ ID NO:4: mutation sites are V239I+R257K:

MTELKQITVLGTGVLGSQIAYQTACHGFDVVAYDINAEVIEKAKARFDSL

AAAYKAENVEGAKEGKADEALQRITYSYDLGEAVAKADLVIEAIPEDIAI

KRDTYEKLATVAPEHTVFATNSSTLLPSDLKEFTGRPEKFLALHFANHVW

VNNTAEVMGTESTDPAVYREVVEFAKNIGMVPIELKKEKAGYVLNSLLVP

LLNAASDLLIDGIADPDMVDKTWRIGTGAPFGPFQIMDIVGLTTVYNISS

QGGEKQKEFADYIKKNYIDEGKLGVAVGDGFYNYKG;

(5) an amino acid sequence shown as SEQ ID NO: 5: mutation sites are V151Q+R257K:

MTELKQITVLGTGVLGSQIAYQTACHGFDVVAYDINAEVIEKAKARFDSL

AAAYKAENVEGAKEGKADEALQRITYSYDLGEAVAKADLVIEAIPEDIAI

KRDTYEKLATVAPEHTVFATNSSTLLPSDLKEFTGRPEKFLALHFANHVW

QNNTAEVMGTESTDPAVYREVVEFAKNIGMVPIELKKEKAGYVLNSLLVP

LLNAASDLLIDGIADPDMVDKTWRIGTGAPFGPFQIMDVVGLTTVYNISS

QGGEKQKEFADYIKKNYIDEGKLGVAVGDGFYNYKG;

or (6) an amino acid sequence shown as SEQ ID NO: 6: mutation sites are I94V+V151Q:

MTELKQITVLGTGVLGSQIAYQTACHGFDVVAYDINAEVIEKAKARFDSL

AAAYKAENVEGAKEGKADEALQRITYSYDLGEAVAKADLVIEAVPEDIAI

KRDTYEKLATVAPEHTVFATNSSTLLPSDLKEFTGRPEKFLALHFANHVW

QNNTAEVMGTESTDPAVYREVVEFAKNIGMVPIELKKEKAGYVLNSLLVP

-continued

LLNAASDLLIDGIADPDMVDKTWRIGTGAPFGPFQIMDVVGLTTVYNISS

QGGEKQREFADYIKKNYIDEGKLGVAVGDGFYNYKG;

a coding DeoxyriboNucleic Acid (DNA) sequence of the DKR mutant includes the following DNA sequences:

(1) SEQ ID NO: 9, which is obtained by mutating TTC into TGG at the site of 691-693 bp in the DKR gene sequence shown as SEQ ID NO: 8;

(2) SEQ ID NO: 10, which is obtained by mutating TTC into TGG at the site of 691-693 bp, and mutating ATT into GTT, GTC, GTA or GTG at the site of 280-282 bp in the DKR gene sequence shown as SEQ ID NO: 8;

(3) SEQ ID NO: 11, which is obtained by mutating TTC into TGG at the site of 691-693 bp, and mutating ATT into GTT, GTC, GTA or GTG at the site of 280-282 bp, and mutating GTC into CAA or CAG at the site of 451-453 bp in the DKR gene sequence shown as SEQ ID NO: 8;

(4) SEQ ID NO: 12, which is obtained by mutating GTC into ATT, ATC or ATA at the site of 751-717 bp, and mutating CGC into AAA or AAG at the site of 769-771 bp in the DKR gene sequence shown as SEQ ID NO: 8;

(5) SEQ ID NO: 13: which is obtained by mutating GTC into CAA or CAG at the site of 451-453 bp, and mutating CGC into AAA or AAG at the site of 769-771 bp in the DKR gene sequence shown as SEQ ID NO: 8;

(6) SEQ ID NO: 14, which is obtained by mutating GTC into CAA or CAG at the site of 451-453 bp, and mutating ATT into GTT, GTC, GTA or GTG at the site of 280-282 bp in the DKR gene sequence shown as SEQ ID NO: 8.

When the mutant of the application is used for preparing the 3R,5S-dihydroxy compound, an ee value of the obtained 3R,5S-dihydroxy compound is higher than 99% and a de value is about 90%. The DKR mutant is a key pharmaceutical intermediate, and particularly provides an efficient catalyst for synthesis of a chiral dihydroxy hexanoate chain of a statin drug, so that the industrial production cost of the 3R,5S-dihydroxy compound is greatly reduced.

DETAILED DESCRIPTION OF THE EMBODIMENTS

Figure 1:
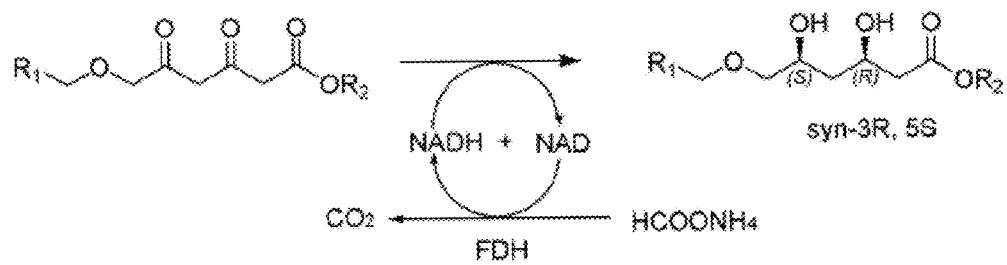
FIG. 1 is a chemical reaction process of synthesis of a 3R,5S-dihydroxy compound according to the application.
Figure 2:
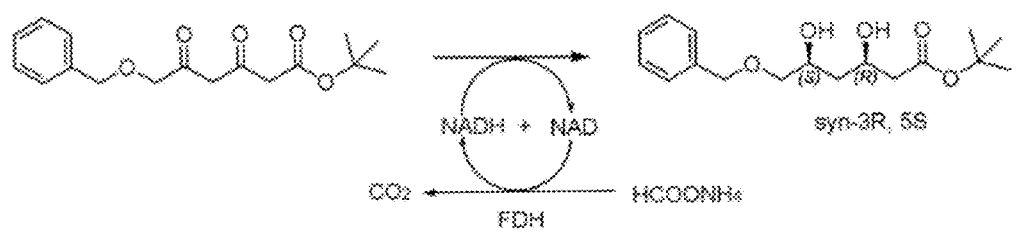
FIG. 2 is a chemical reaction equation of synthesis of 3R,5S-dihydroxy-6-benzyloxy-tert-butyl hexanoate according to the application.
Figure 3:
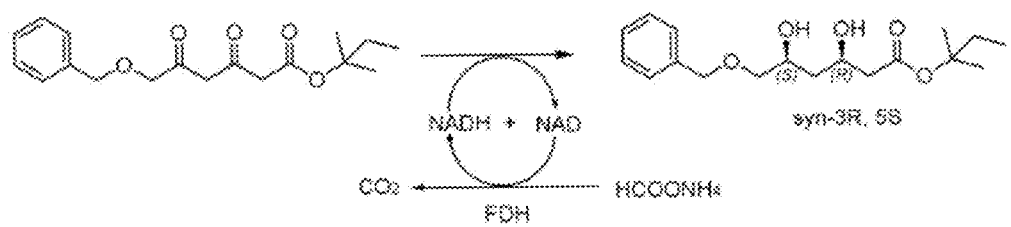
FIG. 3 is a chemical reaction equation of synthesis of 3R,5S-dihydroxy-6-benzyloxy-neopentyl hexanoate according to the application.

In the application, a site-directed saturation mutagenesis method is adopted to mutate a parent DKR gene, thereby changing an amino acid sequence of DKR and implement changing of a protein structure and function, then a DKR mutant with greatly improved enzyme activity is obtained by a directed screening method, and the enzyme activity is improved to be more than twice and even triple that of the parent DKR, thereby greatly reducing industrial production cost of a 3R,5S-dihydroxy compound. In some embodiments, an ee value of an obtained product is higher than 99% and a de value is about 90%.

According to an embodiment of the application, a amount of the DKR mutant of the application used in a process to produce a 3R,5S-dihydroxy compound is only 34% of the amount of DKR coded by a parent gene, and the mutant is suitable for industrial application.

In an embodiment of the application, the site-directed saturation mutagenesis technology is adopted to perform gene mutation by taking a DKR gene derived from a rhodococcuserythropolis SK121 strain as a starting gene, and then the DKR mutant with improved enzyme activity is obtained by a directed screening method. A mutated amino acid residue of the DKR mutant of the application is positioned at a substrate binding site or an area related to substrate and NAD binding and related to NAD proton transfer. For example, 194 is positioned in a NAD binding area and four amino acids (i.e. V151, F231, V239 and R257) are all positioned in the vicinity of the substrate binding site. Changing these amino acids may improve substrate binding specificity, thereby improving enzyme activity. An experimental result of the application shows that single F231W mutation may remarkably improve the activity of the DKR. Further introducing I94V and/or V151Q mutation on the basis of F231W mutation can further improve the activity of the DKR. Combining R257K mutation and V239I or V151Q mutation can also remarkably improve the activity of the DKR.

The obtained DKR mutant can be genetically connected to pET-22b(+) and another expression vector by genetic engineering means, and then excessively expressed in *Escherichia coli*. A molecular weight of the excessively expressed DKR mutant on SDS-PAGE is about 30KD, and a corresponding di-ketone substrate may be reduced in one step under the conditions of 30° C. and pH6.0 to obtain a 3R,5S-dihydroxy compound with higher optical purity.

The di-ketone raw material corresponding to the 3R,5S-dihydroxy compound in the application may be a commercial raw material on the market or an easy-to-prepare ketone compound with the general chemical formula

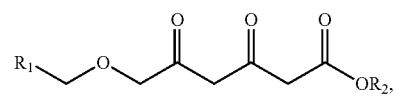

where R1 is selected from an aromatic group, an alkyl group, a naphthenic base, an alkyl-substituted aromatic base, a halogen-substituted aryl, an aromatic heterocycl, a heterocycloalkyl or an alkyl-substituted heterocycloalkyl; and R2 is selected from an alkyl group, a naphthenic base, a haloalkyl group or a halogen naphthenic base. The dihydroxy product is expressed by the following chemical general formula:

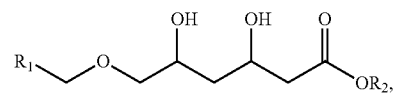

where R1 is selected from an aromatic group, an alkyl group, a naphthenic base, an alkyl-substituted aromatic base, a halogen-substituted aryl, an aromatic heterocycl, a heterocycloalkyl or an alkyl-substituted heterocycloalkyl; and R2 is selected from an alkyl group, a naphthenic base, a haloalkyl group or a halogen naphthenic base.

Definitions

Term "identity" used in the application has a meaning usually known in the field, and those skilled in the art know well rules and standards for measuring identity of different sequences. In the application, sequences limited by different degrees of identity are also required to have improved DKR activity. Those skilled in the art know well a method and means for measure activity of DKR and screen a mutant sequence. Those skilled in the art may easily obtain such a mutant sequence under the guidance of contents of the application. In some embodiments, a sequence of the DKR mutant is an amino acid sequence has identity of at least about 75%, 80%, 85%, 90%, 91%, 92%, 93%, 94%, 95%, 96%, 97%, 98%, 99%, 99.1%, 99.2%, 99.3%, 99.4%, 99.5% or 99.6% with the sequence shown as SEQ ID NO: 7 or 8 and has or codes a protein with improved DKR activity. For example, one or more amino acid residues in the amino acid sequence may be substituted with conservative amino acids, and for example, the one or more amino acid residues are amino acid residues 1, 2, 3, 4, 5, 6, 8, 9, 10, 15, 20, 30, 40 or 50. Conservative amino acids of amino acids are known in the field.

Term "improved DKR activity" used in the application refers to that bioactivity of DKR obtained by the site-directed saturation mutagenesis technology is improved compared with that of starting DKR, for example, catalytic activity improvement, substrate spectrum broadening, thermal stability improvement, pH stability improvement or expression amount increase, and for example, is improved by at least 5%, 10%, 20%, 30%, 40%, 50%, 100%, 150%, 200%, 500% or more compared with that of the starting DKR.

Term "highly stringent condition" used in the application may be defined as follows: (1) weak ionic strength and high temperature are adopted for washing, for example, 0.015M sodium chloride/0.0015M sodium citrate/0.1% sodium dodecyl sulfate, 50° C.; (2) a denaturant such as formamide is adopted in a hybridization process, for example, 50% (v/v) formamide and 0.1% bovine serum albumin/0.1% Ficoll/0.1% polyvinylpyrrolidone/50 mM sodium phosphate buffer solution with pH6.5, including 750 mM sodium chloride and 75 mM sodium citrate, 42° C.; or (3) 50% formamide, 5×SSC (0.75M NaCl and 0.075M sodium citrate), 50 mM sodium phosphate (pH6.8), 0.1% sodium pyrophosphate, 5×Denhardt solution, ultrasonically treated salmon sperm DNA (50 g/ml), 0.1% SDS and 10% dextran sulfate are adopted, 42° C., washing is performed in 0.2× SSC (sodium chloride/sodium citrate) and 50% formamide at 42° C., 55° C., and highly stringent washing is performed in 0.1×SSC containing EDTA at 55° C.

Term "expression cassette" used in the application refers to a linear or ring-shaped nucleic acid molecule, covers DNA and RiboNucleic Acid (RNA) sequences capable of guiding specific nucleotide sequences to be expressed in appropriate host cells, and generally includes a promoter effectively linked with a target polynucleotide, which is randomly effectively linked with a termination signal and/or other regulation elements. The expression cassette may further include sequences required by correct translation of the nucleotide sequences. A coding area usually codes target proteins, and also codes a target functional RNA in a sense or antisense direction, for example, an antisense RNA or a non-translated RNA. An expression cassette including a target polynucleotide sequence may be embedded, referring to that at least one component and at least another component are heterogeneous. An expression cassette may also naturally exist, but is obtained in form of effective recombination for heterogeneous expression.

Term "effectively linked" used in the application refers to such a link manner that a coding nucleotide is at a proper position of a vector to make the coding nucleotide correctly and smoothly copied, transcribed or expressed.

Term "vector" used in the application includes any plasmid, cosmid, bacteriophage or *agrobacterium tumefaciens* binary nucleic acid molecule in a double-stranded or single-stranded linear or ring-shaped form, is preferably a recombinant expression vector, may be a prokaryotic expression vector, may also be a eukaryotic expression vector, and is preferably a prokaryotic expression vector. In some embodiments, the recombinant vector is selected from pET-22b(+), pET-3a(+), pET-3d(+), pET-11a(+), pET-12a(+), pET-14b (+), pET-15b(+), pET-16b(+), pET-17b(+), pET-19b(+), pET-20b(+), pET-21a(+), pET-23a(+), pET-23b(+), pET-24a (+), pET-25b(+), pET-26b(+), pET-27b(+), pET-28a(+), pET-29a(+), pET-30a(+), pET-31 b(+), pET-32a(+), pET-35b (+), pET-38b(+), pET-39b(+), pET-40b(+), pET-41a(+), pET-41b(+), pET-42a(+), pET-43a(+), pET-43b(+), pET-44a (+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19. In some embodiments, the vector is pET-22b(+).

Term "host cell" used in the application includes a prokaryotic cell, a yeast or a high eukaryotic cell. A proper prokaryotic cell includes, but not limited to, a *eubacterium*, such as gram-negative or gram-positive organism, such as *Escherichia coli* of enterobacteriaceae. Various *Escherichia coli* strains can be obtained publicly.

Term "condition of making DKR to act" used in the application refers to a condition capable of making the DKR to catalyze its substrate to be transformed into a corresponding product. In some embodiments, the "condition of making the DKR to act" includes the DKR, the substrate of the DKR, a coenzyme and a proper buffer system.

Term "contact for a period of time" used in the application refers to reacting the DKR mutant with its reaction substrate for enough time under the condition of making the DKR to act to at least partially transform the substrate into a corresponding product.

Those skilled in the art know that although "include" is adopted for expression when the polynucleotide is defined in the application, it does not mean that other sequences unrelated to the function of the polynucleotide may be freely added to two ends of the polynucleotide. Those skilled in the art know that it is necessary to add proper enzyme digesting sites of a restriction enzyme to the two ends of the polynucleotide or add initiator codons, termination codons and the like. Therefore, defining a bispecific tetravalent antibody by adopting a closed expression may not really cover these conditions.

Those skilled in the art all know that one or more codons in a nucleotide sequence may be equivalently substituted under the condition of not changing coded amino acids, and for example, the one or more codons are codons, such as 1, 2, 3, 4, 5, 6, 8, 9, 10, 15, 20, 30, 40 or 50 condons. The codon application table is well-known in the field.

The application will be further described below with nonrestrictive embodiments, those skilled in the art know that many modifications may be made to the application without departing from the spirit of the application, and these modifications also fall within the scope of the application.

The following experimental methods are all conventional methods if there are no special annotations, and adopted experimental materials may all be easily obtained from commercial companies if there are no special annotations. Various antibodies adopted in the following embodiments of the application are all commercial standard antibodies.

EMBODIMENT

Figure 4:
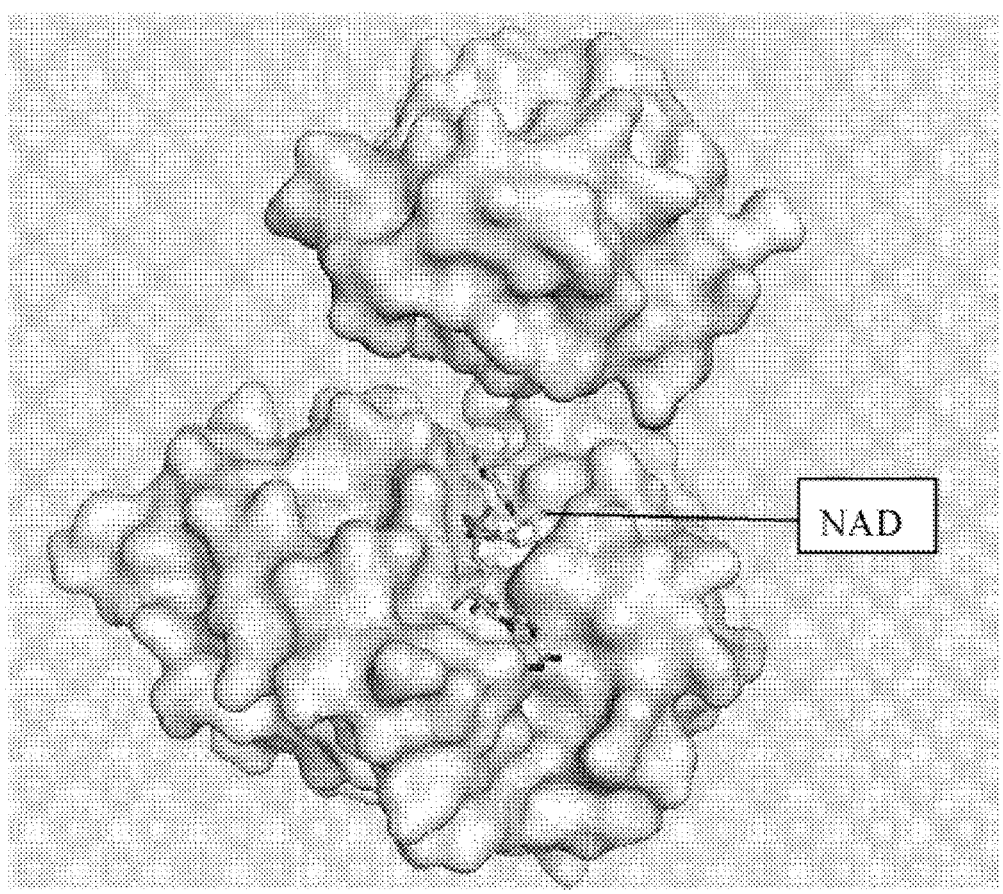
FIG. 4 is a three-dimensional structure mimic diagram of DKR bound with Nicotinamide Adenine Dinucleotide (NAD)

Embodiment 1: Site-Directed Saturation Mutagenesis of DKR (SEQ ID NO: 7) Derived from a *Rhodococcus erythropolis* SK121 Strain An amino acid sequence of the DKR simulates a three-dimensional structure of a protein on website Swiss-model, then binding of a substrate and the protein is simulated by Docking, and Pymol analysis is finally performed to select an amino acid related to substrate and NAD binding and related to NAD proton transfer as a mutated amino acid (FIG. 4).

A corresponding mutation primer (Table 1) is designed by Primmer5.0 according to the mutated amino acid and its flanking sequences (the mutated amino acid refers to mutation site in Table 1). A complete linear fragment is obtained by whole-plasmid Polymerase Chain Reaction (PCR) by taking a pET22b(+) expression vector (purchased from Novagen and with a product number 69744) containing a DKR gene as a template, and after the parent template is removed by DPn I digestion, the PCR product is transferred into *Escherichia coli* BL21 (DE3) and coated in an LB culture dish containing 50 µg/ml ampicillin for culture overnight at 37° C.

TABLE 1

Site-directed saturation mutagenesis primer sequence

| SEQ ID NO. | Mutation site | Primer name | Primer sequence |
|---|---|---|---|
| 15 | I94 | I94-Forward | GGTCATCGAGGCANNNCCCGAGGACATCG |
| 16 | | I94-Reverse | CGATGTCCTCGGGNNNTGCCTCGATGACC |
| 17 | E96 | E96-Forward | GTCATCGAGGCAATTCCCNNNGACATCGCCATCAAGCG |
| 18 | | E96-Reverse | CGCTTGATGGCGATGTCNNNGGGAATTGCCTCGATGAC |
| 19 | R102 | R102-Forward | GAGGACATCGCCATCAAGNNNGACACCTACGAGAAGCTTG |
| 20 | | R102-Reverse | CAAGCTTCTCGTAGGTGTCNNNCTTGATGGCGATGTCCTC |
| 21 | T124 | T124-Forward | CTACCAACTCCTCGNNNCTGCTGCCGAGCG |
| 22 | | T124-Reverse | CGCTCGGCAGCAGNNNCGAGGAGTTGGTAG |
| 23 | S123 | S123-Forward | CGCTACCAACTCCNNNACGCTGCTGCCGAG |
| 24 | | S123-Reverse | CTCGGCAGCAGCGTNNNGGAGTTGGTAGCG |
| 25 | H148 | H148-Forward | CACTTCGCAAATNNNGTGTGGGTCAAC |
| 26 | | H148-Reverse | GTTGACCCACACNNNATTTGCGAAGTGG |
| 27 | V151Q | V151-Forward | CAAATCACGTGTGGNNNAACAACACTGCC |
| 28 | | V151-Reverse | GGCAGTGTTGTTNNNCCACACGTGATTTG |
| 29 | E156 | E156-Forward | CAACAACACTGCCNNNGTCATGGGCACCG |
| 30 | | E156-Reverse | CGGTGCCCATGACNNNGGCAGTGTTGTTG |
| 31 | K189 | K189-Forward | GAACTCAAGAAGGAGNNNGCGGGCTACGTACTC |
| 32 | | K189-Reverse | GAGTACGTAGCCCGCNNNCTCCTTCTTGAGTTC |
| 33 | G191 | G191-Forward | GAACTCAAGAAGGAGAAGGCGNNNTACGTACTCAACTCGC |
| 34 | | G191-Reverse | GCGAGTTGAGTACGTANNNCGCCTTCTCCTTCTTGAGTTC |
| 35 | L194 | L194-Forward | CGGGCTACGTANNNAACTCGCTCCTGG |
| 36 | | L194-Reverse | CCAGGAGCGAGTTNNNTACGTAGCCCG |
| 37 | W223 | W223-Forward | GGTCGACAAGACGNNNCGTATCGGCACCGG |
| 38 | | W223-Reverse | CCGGTGCCGATACGNNNCGTCTTGTCGACC |
| 39 | F231 | F231-Forward | TATCGGCACCGGAGCCCCGNNNGGCCCCTTCCAGATCATG |
| 40 | | F231-Reverse | CATGATCTGGAAGGGGCCNNNCGGGGCTCCGGTGCCGATA |
| 41 | M237 | M237-Forward | GCCCCTTCCAGATCNNNGACGTCGTCGGGTTG |
| 42 | | M237-Reverse | CAACCCGACGACGTCNNNGATCTGGAAGGGGC |
| 43 | V239 | V239-Forward | CTTCCAGATCATGGACNNNGTCGGGTTGACCAC |
| 44 | | V239-Reverse | GTGGTCAACCCGACNNNGTCCATGATCTGGAAG |
| 45 | V240 | V240-Forward | GATCATGGACGTCNNNGGGTTGACCAC |
| 46 | | V240-Reverse | GTGGTCAACCCNNNGACGTCCATGATC |
| 47 | N247 | N247-Forward | GACCACCGTCTACNNNATCTCCTCCCAGG |
| 48 | | N247-Reverse | CCTGGGAGGAGATNNNGTAGACGGTGGTC |
| 49 | Q251 | Q251-Forward | CAACATCTCCTCCNNNGGCGGCGAGAAGC |
| 50 | | Q251-Reverse | GCTTCTCGCCGCCNNNGGAGGAGATGTTG |

TABLE 1-continued

Site-directed saturation mutagenesis primer sequence

| SEQ ID NO. | Mutation site | Primer name | Primer sequence |
|---|---|---|---|
| 51 | R257 | R257-Forward | CCCAGGGCGGCGAGAAGCAGNNNGAATTCGCCGACTACATCAAG |
| 52 | | R257-Reverse | CTTGATGTAGTCGGCGAATTCNNNCTGCTTCTCGCCGCCCTGGG |
| 53 | L273 | L273-Forward | CATCGACGAGGGCAAGNNNGGCGTTGCTGTC |
| 54 | | L273-Reverse | GACAGCAACGCCNNNCTTGCCCTCGTCGATG |
| 55 | A276 | A276-Forward | CGAGGGCAAGCTCGGCGTTNNNGTCGGCGACGGCTTCTAC |
| 56 | | A276-Reverse | GTAGAAGCCGTCGCCGACNNNAACGCCGAGCTTGCCCTCG |

Embodiment 2: Preliminary Screening of a DKR Mutant

According to the contents of embodiment 1, a single colony in the culture dish is selected and inoculated to a 96-deep-hole plate, 0.5 milliliter of LB liquid culture medium containing 50 μg/ml ampicillin is pre-added into each hole, shaking culture is performed for 3 h at 37° C., then IPTG is added until a final concentration is 0.2 mM, induced expression is performed for 16 h at 18° C., centrifugation is performed at 6,000 g for 10 min to collect bacteria, cells of the bacteria are disrupted by an ultrasonic disruptor (JY92-2D, Ningbo Xinzhi Biotechnology Co., Ltd.), centrifugation is performed at 4° C. for 20 min at 10,000 g to obtain supernatant, and activity preliminary screening is performed by virtue of a microplate reader. 30 μl of DMSO is added into the 96-hole plate, 1.5 μl of a main raw material 6-benzyloxy-3,5-dioxo-tert-butyl hexanoate (dissolved in DMSO at 30 mg/ml), 2.5 μl of NADH (20 mg/mL) and 216 μl of a phosphate buffer solution (100 mM, Ph=6.0) are added into a 96-hole plate, background detection is performed at 340 nm, 50 μl of prepared mutant enzyme liquid is added into each hole, and a change of an absorption photometry value at 340 nm is immediately detected at 30° C.

An enzyme activity calculation formula: enzyme activity $(u/mL)=(\Delta A \times 60 \times V_1)/(6.22 \times t \times V_2)$ ΔA: an changed value of absorption photometry in a reaction process;

$V_1$: a total volume of a reaction system;

6.22: an extinction coefficient;

t: detection time of ΔA; and $V_1$: the volume of the added enzyme liquid.

Embodiment 3: Secondary Screening of a DKR Mutant

A mutant of which enzyme activity is higher than that of the parent strain in embodiment 2 is inoculated to 500 ml of LB liquid culture medium containing 50 μg/ml ampicillin, shaking culture is performed at 37° C. until $OD_{600}=0.6$, IPTG is added until a final concentration is 0.2 mM, and induced expression is performed at 18° C. After induction is performed for 16 h, centrifugation is performed at 6,000 g for 10 min to collect bacteria. Cells of the bacteria are disrupted by an ultrasonic disruptor (JY92-2D, Ningbo Xinzhi Biotechnology Co., Ltd.), and centrifugation is performed at 4° C. for 20 min at 10,000 g to obtain supernatant for activity detection. 0.05 g of main raw material

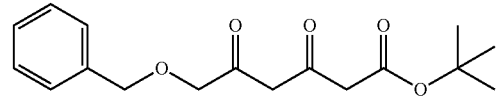 [SMILES: CC(C)(C)OC(=O)CC(=O)CC(=O)COCc1ccccc1]

(6-benzyloxy-3,5-dioxo-tert-butyl hexanoate) and 0.5 ml of polyethylene glycol PEG-400 are added into a 10 ml reaction flask, 4.0 ml of phosphate buffer solution (100 mM, pH=6.0) is added after the raw material is dissolved, and the main raw material is uniformly dispersed in the buffer solution; and 1.5 mg of $NAD^+$, 20.6 mg of ammonium formate, 10 mg of coenzyme formate dehydrogenase and 0.5 ml of DKR are added, the pH of the system is 6.0, and the system temperature is preserved at 30+/−3° C. for 16 h, then Thin Layer Chromatography (TLC) tracking is performed, a system with an obvious transformation product point and an unobvious main raw material point is selected for ethyl acetate extraction, standing is performed for liquid separation, and an organic phase is extracted for High Performance Liquid Chromatography (HPLC) analysis.

Figure 5:
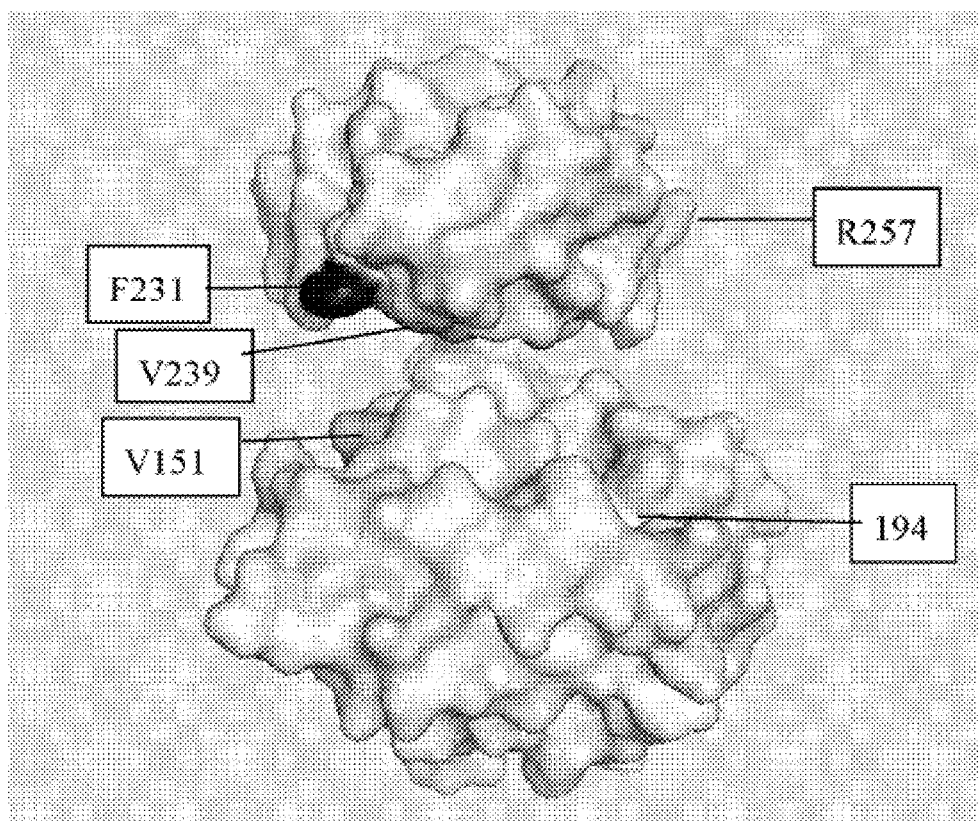
FIG. 5 is a three-dimensional structure mimic diagram of a DKR marking effective mutation sites.

A mutant of which catalytic activity is higher than that of the parent strain is selected for sequencing, mutation site analysis and scale-up culture, repeated measurement of catalytic activity to confirm mutants, and the catalytic activity of mutants F231W (SEQ ID NO: 1), I94V+F231W (SEQ ID NO: 2), I94V+V151Q+F231W (SEQ ID NO: 3), V239I+R257K (SEQ ID NO: 4), V151Q+R257K (SEQ ID NO: 5) and I94V+V151Q (SEQ ID NO: 6) is remarkably improved compared with that of the parent strain, and secondary screening results are shown in Table 2. Computer simulation analysis is performed on a three-dimensional structure of the DKR by adopting software, wherein I94 is positioned in a NAD binding area, four amino acids V151, F231, V239 and R257 are all positioned in the vicinity of substrate binding sites, and changing these amino acids may improve substrate binding specificity, thereby improving enzyme activity (FIG. 5).

TABLE 2

Activity comparison of 3R,5S-dihydroxy-6-benzyloxy-tert-butyl hexanoate prepared by DKR parent strain and mutants

| SEQ ID NO | Site | Enzyme content $^a$ | Transformation | DE % | EE % |
|---|---|---|---|---|---|
| 1 | F231W | 3 wt | 82.70 | 87.66 | 100.00 |
| 2 | I94V + F231W | 2 wt | 72.91 | 89.89 | 100.00 |
| 3 | I94V + V151Q + F231W | 2 wt | 78.31 | 89.44 | 100.00 |
| 4 | V239I + R257K | 2 wt | 68.26 | 85.24 | 100.00 |
| 5 | V151Q + R257K | 2 wt | 62.27 | 88.69 | 100.00 |

TABLE 2-continued

Activity comparison of 3R,5S-dihydroxy-6-benzyloxy-tert-butyl hexanoate prepared by DKR parent strain and mutants

| SEQ ID NO | Site | Enzyme content [a] | Transformation | DE % | EE % |
|---|---|---|---|---|---|
| 6 | I94V + V151Q | 3 wt | 68.46 | 88.14 | 100.00 |
| 7 | parent strain | 6 wt | 62.26 | 87.45 | 100.00 |

[a] refers to a wet weight of recombinant cells of each DKR mutant required by transformation of 1 g substrate; and 1 wt refers to that transformation of 1 g of main raw material requires 1 g of DKR mutant recombinant wet cells.

Embodiment 4: Cloning and Expression of a DKR Mutant

In order to facilitate expression and identification of a DKR mutant, compatible restriction enzyme digesting sites are designed at 5' and 3' ends of its gene. Enzyme digesting is performed respectively on a target gene and pET-22b(+) (other expression plasmids expressing protein in *Escherichia coli* can also be used) at the same time by adopting Nde I and Xho I, connection reaction is performed on larger fragments of the enzyme-digested target gene and plasmid by virtue of T4 DNA ligase, a connection product is transformed into a competent cell of an *Escherichia coli* DH5α strain, and an LB culture flat plate containing 50 μg/ml ampicillin is coated with the transformed competent cell for culture overnight at 37° C.

A single colony grown on the culture dish is selected and inoculated to an LB liquid culture medium containing 50 mg/ml ampicillin, shaking culture is performed overnight at 37° C., bacteria are collected for plasmid extraction, PCR identification and dual-enzyme digestion identification, then a correctly cloned vector is named as pET22b(+)-R-M and transformed into *Escherichia coli* BL21 (DE3), and the LB culture flat plate containing the 50 mg/ml ampicillin is coated with the transformed *Escherichia coli* BL21 (DE3) for culture overnight at 37° C. A single colony grown on the culture flat plate is selected and inoculated to 5 ml of LB liquid culture medium containing 50 mg/ml ampicillin for identification with colony PCR, and subsequent induced expression is performed on *Escherichia coli* containing a correct expression vector. The bacteria liquid is transferred to 500 ml of LB liquid culture medium containing 50 mg/ml ampicillin, shaking culture is performed at 37° C. until $OD_{600}$=0.5~0.6, IPTG is added until the final concentration is 0.2~1.0 mM respectively, induced expression is performed for 10 to 16 h at 18~25° C., the bacteria solution is extracted, centrifugation is performed at 6,000 g for 10 min to collect bacteria, and the bacteria are frozen and preserved for later use at −20° C. Cells of the bacteria are disrupted by an ultrasonic disruptor (JY92-2D, Ningbo Xinzhi Biotechnology Co., Ltd.), centrifugation is performed for 20 min at 10,000 g and 4° C. to obtain supernatant and precipitates, and SDS-PAGE detection is performed on the supernant by virtue of a vertical electrophoresis device. A molecular weight of the expressed DKR mutant on SDS-PAGE is about 30KD.

Embodiment 5: Application of DKR Mutant I94V+F231W to the Preparation of a 3R,5S-Dihydroxy Compound A diketone compound consistent with general formula I

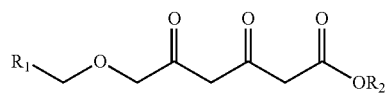

(general formula 1) is selected as an initial raw material, where $R_1$ is selected from an aromatic group, an alkyl group, a naphthenic base, an alkyl-substituted aromatic base, a halogen-substituted aryl, an aromatic heterocycl, a heterocycloalkyl or an alkyl-substituted heterocycloalkyl; and $R_2$ is selected from an alkyl group, a naphthenic base, a haloalkyl group or a halogen naphthenic base. The dihydroxy product is expressed by the following chemical general formula II:

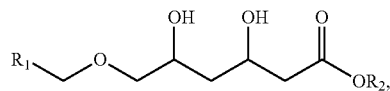

(general formula II)

where $R_1$ is selected from an aromatic group, an alkyl group, a naphthenic base, an alkyl-substituted aromatic base, a halogen-substituted aryl, an aromatic heterocycl, a heterocycloalkyl or an alkyl-substituted heterocycloalkyl; and $R_2$ is selected from an alkyl group, a naphthenic base, a haloalkyl group or a halogen naphthenic base.

(1) application of the DKR mutant I94V+F231W to the preparation of 3R,5S-dihydroxy-6-benzyloxy-tert-butyl hexanoate 5 g of main raw material 6-benzyloxy-3,5-dioxo-tert-butyl hexanoate:

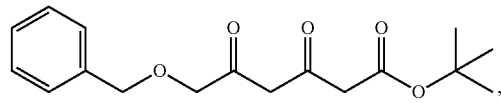 [SMILES: CC(C)(C)OC(=O)CC(=O)CC(=O)COCc1ccccc1]

and 20 ml of polyethylene glycol PEG-400 are added into a 250 ml reaction flask, 160 ml of phosphate buffer solution (100 mM, pH=6.0) is added after the raw materials are dissolved, and the main raw material is uniformly dispersed in the buffer solution; 0.15 g of $NAD^+$, 20.6 g of ammonium formate, 0.25 g of coenzyme formate dehydrogenase and crude enzyme liquid of 2 wt DKR mutant I94V+F231W are added, the pH of the system is 6.0, and temperature is preserved for 17 h at 30+/−3° C.; and reaction is terminated by 200 ml of ethyl acetate, filtration is performed by 125 g of diatomaceous earth, extraction is performed twice with 200 ml of ethyl acetate, standing is performed for liquid separation, and an organic phase is dried, filtered and concentrated to obtain a crude product, wherein a proportion of

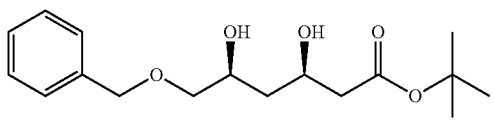 [SMILES: CC(C)(C)OC(=O)C[C@H](O)C[C@H](O)COCc1ccccc1]

(6-benzyloxy-3,5-dioxo-tert-butyl hexanoate) in the system of the product 3R,5S-dihydroxy-6-benzyloxy-tert-butyl hexanoate is 86~91%, the yield is 80~86%, the ee value is higher than 99.5% and the de value is 88~95%.

NMR data of the obtained product is as follows: 400 Hz, $CDCl_3$: δ 7.29 (m, 5H), 4.54 (s, 2H), 4.22 (m, 1H), 4.07 (m, 1H), 3.45~3.40 (m, 4H), 2.41 (d, 2H), 1.65 (t, 2H) and 1.43 (S, 9H).

Catalytic activity over the main raw material 6-benzyloxy-3,5-dioxo-tert-butyl hexanoate and reaction methods of the other five DKR mutants are similar, so as not to be repeatedly described here.

(2) application of the DKR mutant I94V+F231W to preparation of 3R,5S-dihydroxy-6-benzyloxy-neopentyl hexanoate 5 g of main raw material 6-benzyloxy-3,5-dioxo-neopentyl hexanoate:

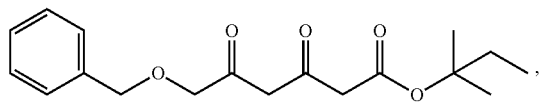 [SMILES: CCC(C)(C)OC(=O)CC(=O)CC(=O)COCc1ccccc1]

and 10 ml of polyethylene glycol PEG-400 are added into a 500 ml reaction flask, 160 ml of phosphate buffer solution (100 mM, pH=6.0) is added after the raw materials are dissolved, and the main raw material is uniformly dispersed in the buffer solution; 0.15 g of $NAD^+$, 20.6 g of ammonium formate, 0.25 g of coenzyme formate dehydrogenase and crude enzyme liquid of 9 wt DKR mutant I94V+F231W are added, the pH of the system is 6.0, and temperature is preserved at 30+/−3° C. for 17 h; and reaction is terminated by 200 ml of ethyl acetate, filtration is performed by 125 g of diatomaceous earth, extraction is performed twice with 200 ml of ethyl acetate, standing is performed for liquid separation, and an organic phase is dried, filtered and concentrated to obtain a crude product, wherein a proportion of

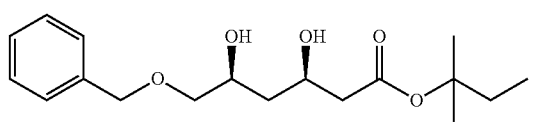 [SMILES: CCC(C)(C)OC(=O)C[C@H](O)C[C@H](O)COCc1ccccc1]

(3R,5S-dihydroxy-6-benzyloxy-neopentyl hexanoate) in the system of the product 3R,5S-dihydroxy-6-benzyloxy-neopentyl hexanoate is 80~90%, the yield is 75~85%, the ee value is higher than 99.3% and the de value is 90~96%.

NMR data of the obtained product is as follows: 400 Hz, $CDCl_3$: 7.26~7.35 ppm (m, 5H), 4.56 ppm (s, 2H), 4.24 ppm (m, 1H), 4.08 ppm (m, 1H), 3.79 ppm (s, 1H), 3.45 ppm (d, 2H), 3.30 ppm (d, 1H), 2.44 ppm (d, 2H), 1.79 ppm (q, 2H), 1.60~1.65 ppm (dd, 2H), 1.43 ppm (s, 6H) and 0.88 ppm (t, 3H).

Catalytic activity over the main raw material 6-benzyloxy-3,5-dioxo-neopentyl hexanoate and reaction methods of the other five DKR mutants are similar, so as not to be repeatedly described here.

What is claimed is:

1. A Diketoreductase (DKR) mutant, comprising the amino acid sequence shown as
SEQ ID NO: 1, SEQ ID NO: 2 or SEQ ID NO: 3.

2. A method for producing a 3R,5S-dihydroxy compound, comprising the following steps: contacting the DKR mutant according to claim 1 with a diketone compound for a period of time, wherein the diketone compound is a compound with general formula I:

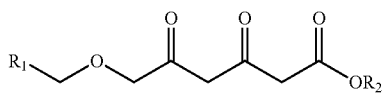

(formula 1)

where $R_1$ is selected from an aromatic group, an alkyl group, a naphthenic base, an alkyl-substituted aromatic base, a halogen-substituted aryl, an aromatic heterocycle, a heterocycloalkyl or an alkyl-substituted heterocycloalkyl and R2 is selected from an alkyl group, a naphthenic base, a haloalkyl group or a halogen naphthenic base.

3. The method for producing the 3R,5S-dihydroxy compound according to claim 2, wherein the diketone compound is selected from 6-benzyloxy-3,5-dioxo-tert-butyl hexanoate, 6-benzyloxy-3,5-dioxo-neopentyl hexanoate, 6-benzyloxy-3,5-dioxo-methyl hexanoate and 6-benzyloxy-3,5-dioxo-ethyl hexanoate.

4. A recombinant vector, comprising a nucleotide sequence encoding the DKR mutant according to claim 1.

5. The recombinant vector according to claim 4, wherein the recombinant vector is a recombinant expression vector.

6. The recombinant vector according to claim 4, wherein the nucleotide sequence comprises a sequence selected from one of SEQ ID NOS: 9-11.

7. A host cell transformed or transfected with the recombinant vector according to claim 4.

* * * * *